United States Patent
Welch et al.

(10) Patent No.: US 7,422,871 B2
(45) Date of Patent: Sep. 9, 2008

(54) **UROPATHOGENIC *E. COLI* D-SERINE DETOXIFICATION OPERON**

(75) Inventors: Rodney A. Welch, Madison, WI (US); Paula L. Roesch, Oregon, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 192 days.

(21) Appl. No.: 11/289,989

(22) Filed: Nov. 30, 2005

(65) Prior Publication Data

US 2006/0099629 A1     May 11, 2006

Related U.S. Application Data

(62) Division of application No. 10/117,417, filed on Apr. 5, 2002, now abandoned.

(60) Provisional application No. 60/281,859, filed on Apr. 5, 2001.

(51) Int. Cl.
    *C12Q 1/04*     (2006.01)
    *C12Q 1/00*     (2006.01)
    *C12Q 1/02*     (2006.01)
    *C12N 1/20*     (2006.01)

(52) U.S. Cl. .............................. 435/34; 435/4; 435/29; 435/243

(58) Field of Classification Search .................. None
See application file for complete search history.

(56) References Cited

U.S. PATENT DOCUMENTS

| | | | |
|---|---|---|---|
| 3,873,269 A | 3/1975 | Kraffczyk et al. | |
| 4,803,170 A | 2/1989 | Stanton et al. | |
| 6,162,827 A | 12/2000 | Javitt | |
| 6,617,488 B1 | 9/2003 | Springer et al. | |

OTHER PUBLICATIONS

Aiyar, S.E., et al., "Upstream A-tracts increase bacterial promoter activity through interactions with the RNA polymerase alpha submit," PNAS (1998) 95(25):14652-14657.

Arthur, M., et al., "Restriction fragment length polymorphisms among uropathogenic *Escherichia coli* isolates: pap-related sequences compared with rrn operons," Inf. Immun. (1990) 58:471-479.

Arthur, M., et al., "Structure and copy number of gene clusters related to the pap P-adhesin operon o furopathogenic *Escherichia coli*," Inf. Immun. (1989) 57(2):314-321.

Arthur, M., et al., Molecular epidemiology of adhesin and hemolysin virulence factors among uropathogenic *Escherichia coli*, Infect. Immun. (1989) 57:303-313.

Bloom, F.R. et al., "Isolation and characterization of D-serine deaminase constitutive mutants by utilization of D-serine as sole carbon or nitrogen source," J. Bacteriol. (1975) 121:1078-1084.

Bloom, F.R. et al., "Positive control in the D-serine deaminase system of *Escherichia coli* K-12," J. Bacteriol. (1975) 121(3):1092-1101.

Bruckner, J. et al., "Quantification of D-amino acids in human urine using GC-MS and HPLC," Amino Acids (1994) 6: 205-211.

Connell, H. et al., "Type 1 fimbrial expression enhances *Escherichia coli* virulence for the urinary tract," PNAS (1996) 93:9827-9832.

Datsenko, K. et al., "One-step inactivation of chromosomal genes in *Escherichia coli* K-12 using PCR products," PNAS (2000) 97(12):6640-6645.

Guzman, L. et al., "Tight regulation, modulation and high-level expression by vectors containing the arabinose P BAD promoter," J. Bacteriol. (1995) 177(14):4121-4130.

Heincz, M.C. et al., "Purification and characterization of D-serine deaminase activator protein," J. Bacteriol. (1984) 160:42-49.

Huang, Y. et al., "Urinary excretion of D-serine in human: comparison of different ages and species," Biol. Pharm. Bull. (1998) 21(2):156-162.

Johnson, J. et al., "P Fimbriae and other virulence factors in *Escherichia coli* urosepsis: association with patients' characteristics," Infect. Dis. (1987) 156:225-229.

Johnson, J. et al., "O, K, and H antigens predict virulence factors, carboxylesterase B pattern, antimicrobial resistance, and host compromise among *Escherichia coli* strains causing urosepsis," J. Infect. Dis. (1994) 169:119-126.

Johnson, J.R. et al., "Aerobactin and other virulence factor genes among strains of *Escherichia coli* causing urosepsis: association with patient characteristics," Infect. Immun. (1988) 56:405-412.

Kinder, S.A. et al., "Cloning of the YenI restriction endonuclease and methyltransferase from *Yersinia enterocolitica* serotype O8.and construction of a transformable R-M+ mutant," Gene (1993) 136:271-275.

Long, A.D. et al., "Improved statistical inference from DNA microarray data using analysis of variance and a bayesian statistical framework," J. Biol. Chem. (2001) 276(23):19937-19944.

McFall, E. et al., "Thermosensitive regualtion of D-serine deaminase synthesis in a mutant of *Escherichia coli* K-12," Molec. Gen. Genetics (1970) 106(4):371-377.

McFall, E., "Dominance studies with stable merodiploids in the D-serine deaminase system of *Escherichia coli* K-12," J. Bacteriol. (1967) 94:1982-1988.

McFall, E., "*Escherichia coli* K-12 mutant forming a temperature-sensitive D-serine deaminase," J. Bacteriol. (1975) 121(3):1074-1077.

McFall, E., "Pleiotropic mutations in the D-serine deaminase system of *Escherichia coli*," J. Mol. Biol. (1964) 9:754-762.

(Continued)

*Primary Examiner*—Mark L Shibuya
(74) *Attorney, Agent, or Firm*—Michael Best & Friedrich LLP

(57) ABSTRACT

Disclosed are methods of detecting uropathogenic *E. coli* genes that are differentially expressed in response to D-serine. Also disclosed are methods of characterizing bacterial isolates from clinical samples based on the ability to metabolize D-serine.

7 Claims, 5 Drawing Sheets

OTHER PUBLICATIONS

McFall, E., "Role of adenosine 3',5'-cyclic monophosphate and its specific binding protein in the regulation of D-serine deaminase synthesis," J. Bacteriol. (1973) 113(2):781-785.

Mobley, H.L.T. et al., "Pyelonephritogenic *Escherichia coli* and killing of cultured human renal proximal tubular epithelial cells: role of hemolysin in some strains," Inf. Immun. (1990) 58:1281-1289.

Mothet, J.P. et al., "D-serine is an endogenous ligand for the glycine site of the N-methyl-D-aspartate receptor," PNAS (2000) 97:4926-4931.

Mulvey, M.A. et al., "Establishment of a persistent *Escherichia coli* reservoir during the acute phase of a bladder infection," Inf. Immun. (2001) 69(7):4572-4579.

Mulvey, M.A. et al., "Induction and evasion of host defenses by type 1-piliated uropathogenic *Escherichia coli*," Science (1998) 282:1494-1497.

Neidhardt, F.C. et al., Culture medium for enterobacteria, J. Bacteriol. (1974) 119:736-747.

Nelson, K.M. et al., "Identification of a locus involved in systemic dissemination of *Yersinia enterocolitica*," Inf. Immun. (2001) 69:6201-6208.

Roesch, P.L. et al., "Chirality sensing: D-serine may be a novel environmental cue used by uropathogenic *Escherichia coli*," ASM 101st General Meeting, Orlando, Florida (2001) Session No. 214/B Abstract B-279.

Sarkar et al., "Screen-printed amperometric biosensors for the rapid measurement of L- and D-amino acids," Analyst (1999) 124:865-870.

Silbernagl et al., "D-serine is reabsorbed in rat renal pars recta," Am. J. Physiol. (1999) 276:F857-863.

Simon, R. et al., "A broad host range mobilization system for in vivo genetic engineering: transposon mutagenesis in gram negative bacteria," Biotechnology (1983) 1:784-791.

Sokurenko, E.V. et al., "Pathogenic adaptation of *Escherichia coli* by natural variation of the FimH adhesin," PNAS (1998) 95:8922-8926.

Torres, A.G. et al., "TonB-dependent systems of uropathogenic *Escherichia coli*: aerobactin and heme transport and tonB are required for virulence in the mouse," Inf. Immun. (2001) 69:6179-6185.

Tsai et al., "D-serine added to clozapine for the treatment of Schizophrenia," Am. J. Psychiatry (1999) 156(11):1822-1825.

Valdivia, R.H. et al., "Fluorescence-based isolation of bacterial genes expressed within host cells," Science (1997) 277:2007-2011.

Wei, Y. et al., "High-density microarray-mediated gene expression profiling of *Escherichia coli*," J. Bacteriol. (2001) 183(2):545-556.

Weyand, N.J. et al., "The essential role of the promoter-proximal subunit of CAP in pap phase variation: Lrp- and helical phase-dependent activation of papBA transcription by CAP from -215," Mol. Micro. (2001) 39(6):1504-1522.

Whittam, T.S. et al., "Clonal relationships among *Escherichia coli* strains that cause hemorrhagic colitis and infantile diarrhea," Inf. Immun. (1993) 61:1619-1629.

Wolosker, H. et al., "Purification of serine racemase: biosynthesis of the neuromodulator D-serine," PNAS (1999) 96:721-725.

SEQUENCE LISTING

<160> NUMBER OF SEQ ID NOS: 18

<210> SEQ ID NO 1
<211> LENGTH: 954
<212> TYPE: DNA
<213> ORGANISM: E. coli CFT073
<220> FEATURE:
<221> NAME/KEY: CDS
<222> LOCATION: (1)..(954)
<223> OTHER INFORMATION: E. coli f-met-tRNA recognizes the triplet
      "GTG" as an initition codon.  The first amino acid
      residue encoded by SEQ ID NO:1 should be a
      methionine residue instead of a valine residue.

<400> SEQUENCE: 1

| gtg att atg gaa ccc ctt cgt gaa ata aga aat cga ctg ctt aac ggc | 48 |
| Val Ile Met Glu Pro Leu Arg Glu Ile Arg Asn Arg Leu Leu Asn Gly | |
| 1               5                   10                  15 | |

| tgg caa cta tca aaa ctg cat act ttt gaa gtg gct gcc agg cat cag | 96 |
| Trp Gln Leu Ser Lys Leu His Thr Phe Glu Val Ala Ala Arg His Gln | |
|         20                  25                  30 | |

| tcc ttc gct ctc gcg gca gag gaa ttg tcg ctg agc ccc agt gcg gta | 144 |
| Ser Phe Ala Leu Ala Ala Glu Glu Leu Ser Leu Ser Pro Ser Ala Val | |
|     35                  40                  45 | |

| agt cac cgt atc aat cag ctg gaa gaa gaa tta ggt att cag ttg ttt | 192 |
| Ser His Arg Ile Asn Gln Leu Glu Glu Glu Leu Gly Ile Gln Leu Phe | |
| 50                  55                  60 | |

| gtt cgt tcc cat cgc aaa gtg gaa tta acg cac gag ggg aaa cgt gtt | 240 |
| Val Arg Ser His Arg Lys Val Glu Leu Thr His Glu Gly Lys Arg Val | |
| 65                  70                  75                  80 | |

| tat tgg gcg cta aaa tcg tcg ctg gat acc ctg aat cag gaa att ctg | 288 |
| Tyr Trp Ala Leu Lys Ser Ser Leu Asp Thr Leu Asn Gln Glu Ile Leu | |
|                 85                  90                  95 | |

| gat atc aaa aat cag gag tta tcg gga acg tta acg ctg tat tcc cgg | 336 |
| Asp Ile Lys Asn Gln Glu Leu Ser Gly Thr Leu Thr Leu Tyr Ser Arg | |
|             100                 105                 110 | |

| ccc tct atc gcc caa tgc tgg ttg gtg ccc gca tta ggt gac ttt aca | 384 |
| Pro Ser Ile Ala Gln Cys Trp Leu Val Pro Ala Leu Gly Asp Phe Thr | |
|         115                 120                 125 | |

| cgc cga tat ccg tct att tcg ctc acc gtg ctc act ggt aat gac aat | 432 |
| Arg Arg Tyr Pro Ser Ile Ser Leu Thr Val Leu Thr Gly Asn Asp Asn | |
|     130                 135                 140 | |

| gtc aat ttg caa cgt gcc gga atc gat ttg gcg atc tac ttt gat gat | 480 |
| Val Asn Leu Gln Arg Ala Gly Ile Asp Leu Ala Ile Tyr Phe Asp Asp | |
| 145                 150                 155                 160 | |

| gcg ccg tca gcg caa ttg gct cat cac ttt ctg atg gat gaa gaa atc | 528 |
| Ala Pro Ser Ala Gln Leu Ala His His Phe Leu Met Asp Glu Glu Ile | |
|                 165                 170                 175 | |

| ttg cca gtt tgc agc ccg gag tac gct caa aga cat gat tta acc aac | 576 |
| Leu Pro Val Cys Ser Pro Glu Tyr Ala Gln Arg His Asp Leu Thr Asn | |
|             180                 185                 190 | |

| acg gta att aac ctg cgt cac tgt acg ttg ctc cat gac aga cag gca | 624 |
| Thr Val Ile Asn Leu Arg His Cys Thr Leu Leu His Asp Arg Gln Ala | |
|         195                 200                 205 | |

| tgg agc aac gac tcc ggt acg gat gaa tgg cat agt tgg gcg caa cat | 672 |
| Trp Ser Asn Asp Ser Gly Thr Asp Glu Trp His Ser Trp Ala Gln His | |
|     210                 215                 220 | |

| tat gcg gtt aat ttg cca aca tct tct gga att ggc ttt gat cgc tct | 720 |
| Tyr Ala Val Asn Leu Pro Thr Ser Ser Gly Ile Gly Phe Asp Arg Ser | |
| 225                 230                 235                 240 | |

```
gat tta gcc gtt atc gcc gcg atg aat cat att ggg gtg gcg atg gga       768
Asp Leu Ala Val Ile Ala Ala Met Asn His Ile Gly Val Ala Met Gly
                245                 250                 255 agg aaa cgt atg gta caa aaa agg ctt gcc agt ggt gag ctc gtc gcg       816
Arg Lys Arg Met Val Gln Lys Arg Leu Ala Ser Gly Glu Leu Val Ala
            260                 265                 270 ccg ttt ggc gat atg acg gtg aaa tgc cat cag cat tat tac atc acc       864
Pro Phe Gly Asp Met Thr Val Lys Cys His Gln His Tyr Tyr Ile Thr
        275                 280                 285 aca tta ccg ggc agg cag tgg cca aaa att gag gca ttt att act tgg       912
Thr Leu Pro Gly Arg Gln Trp Pro Lys Ile Glu Ala Phe Ile Thr Trp
    290                 295                 300 tta aga gaa cag gta agt caa tat gaa tgt tat acc tta taa               954
Leu Arg Glu Gln Val Ser Gln Tyr Glu Cys Tyr Thr Leu
305                 310                 315

<210> SEQ ID NO 2
<211> LENGTH: 317
<212> TYPE: PRT
<213> ORGANISM: E. coli CFT073

<400> SEQUENCE: 2

Val Ile Met Glu Pro Leu Arg Glu Ile Arg Asn Arg Leu Leu Asn Gly
 1               5                   10                  15

Trp Gln Leu Ser Lys Leu His Thr Phe Glu Val Ala Ala Arg His Gln
            20                  25                  30

Ser Phe Ala Leu Ala Ala Glu Glu Leu Ser Leu Ser Pro Ser Ala Val
        35                  40                  45

Ser His Arg Ile Asn Gln Leu Glu Glu Glu Leu Gly Ile Gln Leu Phe
    50                  55                  60

Val Arg Ser His Arg Lys Val Glu Leu Thr His Glu Gly Lys Arg Val
65                  70                  75                  80

Tyr Trp Ala Leu Lys Ser Ser Leu Asp Thr Leu Asn Gln Glu Ile Leu
                85                  90                  95

Asp Ile Lys Asn Gln Glu Leu Ser Gly Thr Leu Thr Leu Tyr Ser Arg
            100                 105                 110

Pro Ser Ile Ala Gln Cys Trp Leu Val Pro Ala Leu Gly Asp Phe Thr
        115                 120                 125

Arg Arg Tyr Pro Ser Ile Ser Leu Thr Val Leu Thr Gly Asn Asp Asn
    130                 135                 140

Val Asn Leu Gln Arg Ala Gly Ile Asp Leu Ala Ile Tyr Phe Asp Asp
145                 150                 155                 160

Ala Pro Ser Ala Gln Leu Ala His His Phe Leu Met Asp Glu Glu Ile
                165                 170                 175

Leu Pro Val Cys Ser Pro Glu Tyr Ala Gln Arg His Asp Leu Thr Asn
            180                 185                 190

Thr Val Ile Asn Leu Arg His Cys Thr Leu Leu His Asp Arg Gln Ala
        195                 200                 205

Trp Ser Asn Asp Ser Gly Thr Asp Glu Trp His Ser Trp Ala Gln His
    210                 215                 220

Tyr Ala Val Asn Leu Pro Thr Ser Ser Gly Ile Gly Phe Asp Arg Ser
225                 230                 235                 240

Asp Leu Ala Val Ile Ala Ala Met Asn His Ile Gly Val Ala Met Gly
                245                 250                 255

Arg Lys Arg Met Val Gln Lys Arg Leu Ala Ser Gly Glu Leu Val Ala
            260                 265                 270
```

| | | | | | | | | | | | | | | | | |
|---|---|---|---|---|---|---|---|---|---|---|---|---|---|---|---|---|
| Pro | Phe | Gly | Asp | Met | Thr | Val | Lys | Cys | His | Gln | His | Tyr | Tyr | Ile | Thr | |
| | | 275 | | | | 280 | | | | 285 | | | | | | |
| Thr | Leu | Pro | Gly | Arg | Gln | Trp | Pro | Lys | Ile | Glu | Ala | Phe | Ile | Thr | Trp | |
| | 290 | | | | | 295 | | | | 300 | | | | | | |
| Leu | Arg | Glu | Gln | Val | Ser | Gln | Tyr | Glu | Cys | Tyr | Thr | Leu | | | | |
| 305 | | | | | 310 | | | | | 315 | | | | | | |

<210> SEQ ID NO 3
<211> LENGTH: 1338
<212> TYPE: DNA
<213> ORGANISM: E. coli CFT073
<220> FEATURE:
<221> NAME/KEY: CDS
<222> LOCATION: (1)..(1338)

<400> SEQUENCE: 3

| | | | | | | | | | | | | | | | | |
|---|---|---|---|---|---|---|---|---|---|---|---|---|---|---|---|---|
| atg | cac | tct | caa | atc | tgg | gtt | gtg | agc | acg | ctg | ctt | atc | agc | atc | gtg | 48 |
| Met | His | Ser | Gln | Ile | Trp | Val | Val | Ser | Thr | Leu | Leu | Ile | Ser | Ile | Val | |
| 1 | | | | 5 | | | | | 10 | | | | | 15 | | |
| tta | att | gta | ctg | acc | atc | gtg | aag | ttc | aaa | ttc | cac | ccg | ttt | ctg | gcg | 96 |
| Leu | Ile | Val | Leu | Thr | Ile | Val | Lys | Phe | Lys | Phe | His | Pro | Phe | Leu | Ala | |
| | | | 20 | | | | | 25 | | | | | 30 | | | |
| ctg | ttg | ctg | gcc | agc | ttc | ttc | gtg | gga | acg | atg | atg | ggc | atg | ggg | cca | 144 |
| Leu | Leu | Leu | Ala | Ser | Phe | Phe | Val | Gly | Thr | Met | Met | Gly | Met | Gly | Pro | |
| | | 35 | | | | | 40 | | | | | 45 | | | | |
| ctg | gat | atg | gta | aat | gct | att | gaa | agt | gga | att | ggc | gga | acg | ctg | ggg | 192 |
| Leu | Asp | Met | Val | Asn | Ala | Ile | Glu | Ser | Gly | Ile | Gly | Gly | Thr | Leu | Gly | |
| | 50 | | | | | 55 | | | | | 60 | | | | | |
| ttc | ctc | gct | gcg | gtt | atc | ggc | ctt | ggc | acg | ata | ctg | gga | aaa | atg | atg | 240 |
| Phe | Leu | Ala | Ala | Val | Ile | Gly | Leu | Gly | Thr | Ile | Leu | Gly | Lys | Met | Met | |
| 65 | | | | | 70 | | | | | 75 | | | | | 80 | |
| gaa | gta | tcc | ggg | gcc | gca | gaa | aga | att | ggt | ctg | aca | ctt | caa | cgc | tgc | 288 |
| Glu | Val | Ser | Gly | Ala | Ala | Glu | Arg | Ile | Gly | Leu | Thr | Leu | Gln | Arg | Cys | |
| | | | | 85 | | | | | 90 | | | | | 95 | | |
| cgg | tgg | ctt | tca | gct | gat | gtc | att | atg | gtg | ctg | gtt | ggc | ctg | att | tgc | 336 |
| Arg | Trp | Leu | Ser | Ala | Asp | Val | Ile | Met | Val | Leu | Val | Gly | Leu | Ile | Cys | |
| | | | 100 | | | | | 105 | | | | | 110 | | | |
| ggc | atc | acg | ctg | ttt | gtt | gaa | gtg | ggc | gtc | gtg | cta | ttg | att | cct | ctg | 384 |
| Gly | Ile | Thr | Leu | Phe | Val | Glu | Val | Gly | Val | Val | Leu | Leu | Ile | Pro | Leu | |
| | | 115 | | | | | 120 | | | | | 125 | | | | |
| gct | ttt | tca | att | gcc | aaa | aaa | acc | aat | acc | tca | ttg | tta | aag | ctg | gcc | 432 |
| Ala | Phe | Ser | Ile | Ala | Lys | Lys | Thr | Asn | Thr | Ser | Leu | Leu | Lys | Leu | Ala | |
| | 130 | | | | | 135 | | | | | 140 | | | | | |
| att | ccg | ctg | tgt | acc | gca | ttg | atg | gca | gtg | cac | tgc | gtg | gtt | ccc | cca | 480 |
| Ile | Pro | Leu | Cys | Thr | Ala | Leu | Met | Ala | Val | His | Cys | Val | Val | Pro | Pro | |
| 145 | | | | | 150 | | | | | 155 | | | | | 160 | |
| cat | ccg | gct | gct | tta | tat | gtt | gcc | aat | aag | ctg | ggc | gca | gat | atc | ggt | 528 |
| His | Pro | Ala | Ala | Leu | Tyr | Val | Ala | Asn | Lys | Leu | Gly | Ala | Asp | Ile | Gly | |
| | | | | 165 | | | | | 170 | | | | | 175 | | |
| tcg | gtg | atc | gtc | tac | ggt | ttg | ctg | gtt | ggg | ctg | atg | gca | tca | ctg | atc | 576 |
| Ser | Val | Ile | Val | Tyr | Gly | Leu | Leu | Val | Gly | Leu | Met | Ala | Ser | Leu | Ile | |
| | | | 180 | | | | | 185 | | | | | 190 | | | |
| ggt | ggc | cca | ctt | ttc | ctt | aaa | ttt | ctg | ggt | caa | cga | ctg | ccc | ttt | aaa | 624 |
| Gly | Gly | Pro | Leu | Phe | Leu | Lys | Phe | Leu | Gly | Gln | Arg | Leu | Pro | Phe | Lys | |
| | | 195 | | | | | 200 | | | | | 205 | | | | |
| cct | gta | ccc | aca | gag | ttt | gcc | gat | ctc | aaa | gtt | cgc | gat | gaa | aaa | aca | 672 |
| Pro | Val | Pro | Thr | Glu | Phe | Ala | Asp | Leu | Lys | Val | Arg | Asp | Glu | Lys | Thr | |
| | 210 | | | | | 215 | | | | | 220 | | | | | |
| cta | ccg | tca | tta | ggc | gca | acg | tta | ttc | acc | gta | ctg | cta | ccc | att | gcg | 720 |
| Leu | Pro | Ser | Leu | Gly | Ala | Thr | Leu | Phe | Thr | Val | Leu | Leu | Pro | Ile | Ala | |
| 225 | | | | | 230 | | | | | 235 | | | | | 240 | |

```
ctg atg ttg gtt aaa acg att gcc gaa ttg aat atg gca cgt gag agt       768
Leu Met Leu Val Lys Thr Ile Ala Glu Leu Asn Met Ala Arg Glu Ser
            245                 250                 255 ggt ttg tat acc ttg ctt gag ttt att ggc aac cct atc act gcc acg       816
Gly Leu Tyr Thr Leu Leu Glu Phe Ile Gly Asn Pro Ile Thr Ala Thr
        260                 265                 270 ttt atc gcc gtg ttt gtc gcc tat tat gtg ttg ggt ata cgt cag cat       864
Phe Ile Ala Val Phe Val Ala Tyr Tyr Val Leu Gly Ile Arg Gln His
        275                 280                 285 atg agc atg ggg acg atg ctc aca cat acg gaa aat ggt ttc ggt tct       912
Met Ser Met Gly Thr Met Leu Thr His Thr Glu Asn Gly Phe Gly Ser
        290                 295                 300 att gct aat att ttg ctg att atc ggg gcc gga ggc gca ttc aac gcc       960
Ile Ala Asn Ile Leu Leu Ile Ile Gly Ala Gly Gly Ala Phe Asn Ala
305                 310                 315                 320 att tta aaa agc agc agt ctc gct gat acg ctg gca gtt att ctc tcc      1008
Ile Leu Lys Ser Ser Ser Leu Ala Asp Thr Leu Ala Val Ile Leu Ser
                325                 330                 335 aat atg cat atg cac ccg att ctt ctg gcc tgg ttg gtg gca ctt att      1056
Asn Met His Met His Pro Ile Leu Leu Ala Trp Leu Val Ala Leu Ile
                340                 345                 350 ctg cat gct gca gtg ggc tcc gct acg gtg gca atg atg ggg gca acg      1104
Leu His Ala Ala Val Gly Ser Ala Thr Val Ala Met Met Gly Ala Thr
            355                 360                 365 gca att gtt gca ccc atg ctg ccg ctg tat ccc gac atc agc ccg gaa      1152
Ala Ile Val Ala Pro Met Leu Pro Leu Tyr Pro Asp Ile Ser Pro Glu
        370                 375                 380 att att gcg att gct atc ggt tcc ggt gcg att ggc tgc acg atc gtt      1200
Ile Ile Ala Ile Ala Ile Gly Ser Gly Ala Ile Gly Cys Thr Ile Val
385                 390                 395                 400 acg gac tca ctt ttc tgg ctg gtg aag caa tat tgc ggc gct acg ctc      1248
Thr Asp Ser Leu Phe Trp Leu Val Lys Gln Tyr Cys Gly Ala Thr Leu
                405                 410                 415 aat gaa aca ttt aaa tac tat acg aca gcg aca ttt atc gct tca gtc      1296
Asn Glu Thr Phe Lys Tyr Tyr Thr Thr Ala Thr Phe Ile Ala Ser Val
                420                 425                 430 atc gct ctg gcg ggc aca ttc ctg ctg tca ttt atc atc taa              1338
Ile Ala Leu Ala Gly Thr Phe Leu Leu Ser Phe Ile Ile
            435                 440                 445

<210> SEQ ID NO 4
<211> LENGTH: 445
<212> TYPE: PRT
<213> ORGANISM: E. coli CFT073

<400> SEQUENCE: 4

Met His Ser Gln Ile Trp Val Val Ser Thr Leu Leu Ile Ser Ile Val
 1               5                  10                  15

Leu Ile Val Leu Thr Ile Val Lys Phe Lys Phe His Pro Phe Leu Ala
                20                  25                  30

Leu Leu Leu Ala Ser Phe Phe Val Gly Thr Met Met Gly Met Gly Pro
            35                  40                  45

Leu Asp Met Val Asn Ala Ile Glu Ser Gly Ile Gly Gly Thr Leu Gly
        50                  55                  60

Phe Leu Ala Ala Val Ile Gly Leu Gly Thr Ile Leu Gly Lys Met Met
65                  70                  75                  80

Glu Val Ser Gly Ala Ala Glu Arg Ile Gly Leu Thr Leu Gln Arg Cys
                85                  90                  95
```

```
Arg Trp Leu Ser Ala Asp Val Ile Met Val Leu Val Gly Leu Ile Cys
            100                 105                 110

Gly Ile Thr Leu Phe Val Glu Val Gly Val Leu Leu Ile Pro Leu
        115                 120                 125

Ala Phe Ser Ile Ala Lys Lys Thr Asn Thr Ser Leu Leu Lys Leu Ala
    130                 135                 140

Ile Pro Leu Cys Thr Ala Leu Met Ala Val His Cys Val Pro Pro
145                 150                 155                 160

His Pro Ala Ala Leu Tyr Val Ala Asn Lys Leu Gly Ala Asp Ile Gly
                165                 170                 175

Ser Val Ile Val Tyr Gly Leu Leu Val Gly Leu Met Ala Ser Leu Ile
            180                 185                 190

Gly Gly Pro Leu Phe Leu Lys Phe Leu Gly Gln Arg Leu Pro Phe Lys
        195                 200                 205

Pro Val Pro Thr Glu Phe Ala Asp Leu Lys Val Arg Asp Glu Lys Thr
    210                 215                 220

Leu Pro Ser Leu Gly Ala Thr Leu Phe Thr Val Leu Leu Pro Ile Ala
225                 230                 235                 240

Leu Met Leu Val Lys Thr Ile Ala Glu Leu Asn Met Ala Arg Glu Ser
                245                 250                 255

Gly Leu Tyr Thr Leu Leu Glu Phe Ile Gly Asn Pro Ile Thr Ala Thr
            260                 265                 270

Phe Ile Ala Val Phe Val Ala Tyr Tyr Val Leu Gly Ile Arg Gln His
        275                 280                 285

Met Ser Met Gly Thr Met Leu Thr His Thr Glu Asn Gly Phe Gly Ser
    290                 295                 300

Ile Ala Asn Ile Leu Leu Ile Ile Gly Ala Gly Gly Ala Phe Asn Ala
305                 310                 315                 320

Ile Leu Lys Ser Ser Ser Leu Ala Asp Thr Leu Ala Val Ile Leu Ser
                325                 330                 335

Asn Met His Met His Pro Ile Leu Leu Ala Trp Leu Val Ala Leu Ile
            340                 345                 350

Leu His Ala Ala Val Gly Ser Ala Thr Val Ala Met Met Gly Ala Thr
        355                 360                 365

Ala Ile Val Ala Pro Met Leu Pro Leu Tyr Pro Asp Ile Ser Pro Glu
    370                 375                 380

Ile Ile Ala Ile Ala Ile Gly Ser Gly Ala Ile Gly Cys Thr Ile Val
385                 390                 395                 400

Thr Asp Ser Leu Phe Trp Leu Val Lys Gln Tyr Cys Gly Ala Thr Leu
                405                 410                 415

Asn Glu Thr Phe Lys Tyr Tyr Thr Thr Ala Thr Phe Ile Ala Ser Val
            420                 425                 430

Ile Ala Leu Ala Gly Thr Phe Leu Leu Ser Phe Ile Ile
        435                 440                 445

<210> SEQ ID NO 5
<211> LENGTH: 1329
<212> TYPE: DNA
<213> ORGANISM: E. coli CFT073
<220> FEATURE:
<221> NAME/KEY: CDS
<222> LOCATION: (1)..(1329)

<400> SEQUENCE: 5 atg gaa aac gct aaa atg aat tcg ctc atc gcc cag tat ccg ttg gta    48
Met Glu Asn Ala Lys Met Asn Ser Leu Ile Ala Gln Tyr Pro Leu Val
```

-continued

```
         1               5              10              15
gag gat ctg gtt gct ctt aaa gaa acc acc tgg ttt aat cct ggc acg        96
Glu Asp Leu Val Ala Leu Lys Glu Thr Thr Trp Phe Asn Pro Gly Thr
                     20              25              30 acc tca ttg gca gaa ggt tta cct tat gtt ggc ctg acc gaa cag gat       144
Thr Ser Leu Ala Glu Gly Leu Pro Tyr Val Gly Leu Thr Glu Gln Asp
             35              40              45 gtt cag gac gcc cat gcg cgc ctg tct cgt ttt gcg ccg tat ctg gca       192
Val Gln Asp Ala His Ala Arg Leu Ser Arg Phe Ala Pro Tyr Leu Ala
 50              55              60 aaa gca ttt cct gaa acg gct gcc gcg ggg ggg att att gaa tca gaa       240
Lys Ala Phe Pro Glu Thr Ala Ala Ala Gly Gly Ile Ile Glu Ser Glu
 65              70              75              80 ctg gtt gct att cct gct atg caa aaa cgg ctg gaa aag gaa tat caa       288
Leu Val Ala Ile Pro Ala Met Gln Lys Arg Leu Glu Lys Glu Tyr Gln
                 85              90              95 caa ccg atc gcc ggg caa ttg cta cta aaa aaa gac agc cat ttg ccg       336
Gln Pro Ile Ala Gly Gln Leu Leu Leu Lys Lys Asp Ser His Leu Pro
            100             105             110 att tcc ggc tcc ata aaa gca cgt ggc ggg att tat gaa gtc ctg gcc       384
Ile Ser Gly Ser Ile Lys Ala Arg Gly Gly Ile Tyr Glu Val Leu Ala
        115             120             125 cat gct gaa aaa ctg gct ctg gaa gcg ggt ttg ctg aca ctt gag gat       432
His Ala Glu Lys Leu Ala Leu Glu Ala Gly Leu Leu Thr Leu Glu Asp
130             135             140 gat tac agc aaa ctg ctt tcc ccg gag ttt aaa cag ttc ttt agc caa       480
Asp Tyr Ser Lys Leu Leu Ser Pro Glu Phe Lys Gln Phe Phe Ser Gln
145             150             155             160 tac agt att gct gtg gga tca acc gga aat ctg ggg tta tca att ggt       528
Tyr Ser Ile Ala Val Gly Ser Thr Gly Asn Leu Gly Leu Ser Ile Gly
                165             170             175 att atg agc gcc cgc atc ggc ttt aaa gta acg gtg cat atg tct gct       576
Ile Met Ser Ala Arg Ile Gly Phe Lys Val Thr Val His Met Ser Ala
            180             185             190 gat gcc cgc gcc tgg aaa aaa gcg aaa ctg cgc agt cat ggc gtt act       624
Asp Ala Arg Ala Trp Lys Lys Ala Lys Leu Arg Ser His Gly Val Thr
        195             200             205 gtc gtg gaa tac gag caa gat tat ggt gtt gcc gtc gag gaa gga cgt       672
Val Val Glu Tyr Glu Gln Asp Tyr Gly Val Ala Val Glu Glu Gly Arg
210             215             220 aaa gcc gcg cag tct gac ccg aac tgt ttc ttt att gat gac gaa aat       720
Lys Ala Ala Gln Ser Asp Pro Asn Cys Phe Phe Ile Asp Asp Glu Asn
225             230             235             240 tcc cgc acg ttg ttc ctt gga tat tcc gtc gca ggc cag cgt ctt aag       768
Ser Arg Thr Leu Phe Leu Gly Tyr Ser Val Ala Gly Gln Arg Leu Lys
                245             250             255 gcg caa ttt gct cag caa ggt cgc atc gtc gat gct gat aac cct ctg       816
Ala Gln Phe Ala Gln Gln Gly Arg Ile Val Asp Ala Asp Asn Pro Leu
            260             265             270 ttt gtc tat ctg ccg tgt ggt gtt ggc ggt ggt cct ggt ggc gtc gca       864
Phe Val Tyr Leu Pro Cys Gly Val Gly Gly Gly Pro Gly Gly Val Ala
        275             280             285 ttc gga ctt aaa ctg gcg ttt ggc gat cat gtt cac tgc ttt ttt gcc       912
Phe Gly Leu Lys Leu Ala Phe Gly Asp His Val His Cys Phe Phe Ala
290             295             300 gaa cca aca cac tcc ccg tgt atg tta tta ggc gtc cat acc gga tta       960
Glu Pro Thr His Ser Pro Cys Met Leu Leu Gly Val His Thr Gly Leu
305             310             315             320 cac gat cag att tct gtt cag gat att ggc atc gac aac ctt acc gct      1008
```

```
His Asp Gln Ile Ser Val Gln Asp Ile Gly Ile Asp Asn Leu Thr Ala
            325                 330                 335 gcc gat ggc ctt gca gtt ggt cgc gca tcg ggc ttt gtc ggg cgg gca      1056
Ala Asp Gly Leu Ala Val Gly Arg Ala Ser Gly Phe Val Gly Arg Ala
            340                 345                 350 atg gag cgt ctg ctg gat ggt ttc tat acc ctt agc gat caa acc atg      1104
Met Glu Arg Leu Leu Asp Gly Phe Tyr Thr Leu Ser Asp Gln Thr Met
            355                 360                 365 tat gac atg ctt ggc tgg ctg gcg cag gaa gaa ggt att cgt ctt gaa      1152
Tyr Asp Met Leu Gly Trp Leu Ala Gln Glu Glu Gly Ile Arg Leu Glu
        370                 375                 380 cca tcg gca ctg gcg ggt atg gcc ggg tct cag cgc gtg tgc gca tca      1200
Pro Ser Ala Leu Ala Gly Met Ala Gly Ser Gln Arg Val Cys Ala Ser
385                 390                 395                 400 gta agt tac caa cag atg cac ggt ttc agc gcc gaa caa ctg cgt aat      1248
Val Ser Tyr Gln Gln Met His Gly Phe Ser Ala Glu Gln Leu Arg Asn
                405                 410                 415 gcc act cat ctg gtg tgg gcg acg gga ggt gga atg gtg ccg gaa gaa      1296
Ala Thr His Leu Val Trp Ala Thr Gly Gly Gly Met Val Pro Glu Glu
            420                 425                 430 gag atg aat caa tat ctg gca aaa ggc cgt taa                          1329
Glu Met Asn Gln Tyr Leu Ala Lys Gly Arg
            435                 440

<210> SEQ ID NO 6
<211> LENGTH: 442
<212> TYPE: PRT
<213> ORGANISM: E. coli CFT073

<400> SEQUENCE: 6

Met Glu Asn Ala Lys Met Asn Ser Leu Ile Ala Gln Tyr Pro Leu Val
 1               5                  10                  15

Glu Asp Leu Val Ala Leu Lys Glu Thr Thr Trp Phe Asn Pro Gly Thr
             20                  25                  30

Thr Ser Leu Ala Glu Gly Leu Pro Tyr Val Gly Leu Thr Glu Gln Asp
         35                  40                  45

Val Gln Asp Ala His Ala Arg Leu Ser Arg Phe Ala Pro Tyr Leu Ala
     50                  55                  60

Lys Ala Phe Pro Glu Thr Ala Ala Gly Gly Ile Ile Glu Ser Glu
 65                  70                  75                  80

Leu Val Ala Ile Pro Ala Met Gln Lys Arg Leu Glu Lys Glu Tyr Gln
                 85                  90                  95

Gln Pro Ile Ala Gly Gln Leu Leu Lys Lys Asp Ser His Leu Pro
            100                 105                 110

Ile Ser Gly Ser Ile Lys Ala Arg Gly Gly Ile Tyr Glu Val Leu Ala
        115                 120                 125

His Ala Glu Lys Leu Ala Leu Glu Ala Gly Leu Leu Thr Leu Glu Asp
    130                 135                 140

Asp Tyr Ser Lys Leu Leu Ser Pro Glu Phe Lys Gln Phe Phe Ser Gln
145                 150                 155                 160

Tyr Ser Ile Ala Val Gly Ser Thr Gly Asn Leu Gly Leu Ser Ile Gly
                165                 170                 175

Ile Met Ser Ala Arg Ile Gly Phe Lys Val Thr Val His Met Ser Ala
            180                 185                 190

Asp Ala Arg Ala Trp Lys Lys Ala Lys Leu Arg Ser His Gly Val Thr
        195                 200                 205

Val Val Glu Tyr Glu Gln Asp Tyr Gly Val Ala Val Glu Glu Gly Arg
```

-continued

```
                    210                 215                 220
Lys Ala Ala Gln Ser Asp Pro Asn Cys Phe Phe Ile Asp Asp Glu Asn
225                 230                 235                 240

Ser Arg Thr Leu Phe Leu Gly Tyr Ser Val Ala Gly Gln Arg Leu Lys
                245                 250                 255

Ala Gln Phe Ala Gln Gln Gly Arg Ile Val Asp Ala Asp Asn Pro Leu
                260                 265                 270

Phe Val Tyr Leu Pro Cys Gly Val Gly Gly Pro Gly Val Ala
                275                 280                 285

Phe Gly Leu Lys Leu Ala Phe Gly Asp His Val His Cys Phe Phe Ala
                290                 295                 300

Glu Pro Thr His Ser Pro Cys Met Leu Leu Gly Val His Thr Gly Leu
305                 310                 315                 320

His Asp Gln Ile Ser Val Gln Asp Ile Gly Ile Asp Asn Leu Thr Ala
                325                 330                 335

Ala Asp Gly Leu Ala Val Gly Arg Ala Ser Gly Phe Val Gly Arg Ala
                340                 345                 350

Met Glu Arg Leu Leu Asp Gly Phe Tyr Thr Leu Ser Asp Gln Thr Met
                355                 360                 365

Tyr Asp Met Leu Gly Trp Leu Ala Gln Glu Glu Gly Ile Arg Leu Glu
                370                 375                 380

Pro Ser Ala Leu Ala Gly Met Ala Gly Ser Gln Arg Val Cys Ala Ser
385                 390                 395                 400

Val Ser Tyr Gln Gln Met His Gly Phe Ser Ala Glu Gln Leu Arg Asn
                405                 410                 415

Ala Thr His Leu Val Trp Ala Thr Gly Gly Gly Met Val Pro Glu Glu
                420                 425                 430

Glu Met Asn Gln Tyr Leu Ala Lys Gly Arg
                435                 440

<210> SEQ ID NO 7
<211> LENGTH: 630
<212> TYPE: DNA
<213> ORGANISM: E. coli CFT073
<220> FEATURE:
<221> NAME/KEY: CDS
<222> LOCATION: (1)..(630)

<400> SEQUENCE: 7 atg caa aac aga aaa ttt tta acg cat cat gaa att aat tta cta ctt        48
Met Gln Asn Arg Lys Phe Leu Thr His His Glu Ile Asn Leu Leu Leu
  1               5                  10                  15 caa tct gta aaa caa aag agt tgc tct tca cgc gat gtt tgc atg att        96
Gln Ser Val Lys Gln Lys Ser Cys Ser Ser Arg Asp Val Cys Met Ile
             20                  25                  30 tta ttg gct tat ttt cat ggt ctg cgt gtt agt gag ctc tta tct ctg       144
Leu Leu Ala Tyr Phe His Gly Leu Arg Val Ser Glu Leu Leu Ser Leu
         35                  40                  45 cag ttg tcg gat tta gaa cta act aca gaa aaa ata tat att caa cgg       192
Gln Leu Ser Asp Leu Glu Leu Thr Thr Glu Lys Ile Tyr Ile Gln Arg
     50                  55                  60 ata aaa aat gga ttc agt aca gtc cat cca ctt caa aag gaa gag gtg       240
Ile Lys Asn Gly Phe Ser Thr Val His Pro Leu Gln Lys Glu Glu Val
 65                  70                  75                  80 att gca ata aca aac tgg ctg aat gaa agg aat tca tta aat gtt aaa       288
Ile Ala Ile Thr Asn Trp Leu Asn Glu Arg Asn Ser Leu Asn Val Lys
                 85                  90                  95
```

```
cat ttc aat gat aac ccg tgg tta ttt gtt tcc cga aca gga aaa cca    336
His Phe Asn Asp Asn Pro Trp Leu Phe Val Ser Arg Thr Gly Lys Pro
        100                 105                 110 tta tcg aga caa cga ttt tat aac ata gtt tct gct gcg ggt aaa aat    384
Leu Ser Arg Gln Arg Phe Tyr Asn Ile Val Ser Ala Ala Gly Lys Asn
        115                 120                 125 gca ggt tta aat att aaa gtt cat cca cat atg tta cgc cat gca tgt    432
Ala Gly Leu Asn Ile Lys Val His Pro His Met Leu Arg His Ala Cys
130                 135                 140 ggt tat tca cta gca gat aat ggt gtg gat acc cgt ctt att cag gac    480
Gly Tyr Ser Leu Ala Asp Asn Gly Val Asp Thr Arg Leu Ile Gln Asp
145                 150                 155                 160 tat ctc ggg cat cgt aat atc agg cat acg gta att tat act gct tct    528
Tyr Leu Gly His Arg Asn Ile Arg His Thr Val Ile Tyr Thr Ala Ser
            165                 170                 175 aat tca atg aga ttt gaa aaa atg tgg ggg ata ggt gac gca aaa aag    576
Asn Ser Met Arg Phe Glu Lys Met Trp Gly Ile Gly Asp Ala Lys Lys
            180                 185                 190 caa cat ttt gac cca aaa tgt aaa ccc aat ctt tgt tta gaa att ctc    624
Gln His Phe Asp Pro Lys Cys Lys Pro Asn Leu Cys Leu Glu Ile Leu
            195                 200                 205 gta tag                                                            630
Val
210

<210> SEQ ID NO 8
<211> LENGTH: 209
<212> TYPE: PRT
<213> ORGANISM: E. coli CFT073

<400> SEQUENCE: 8

Met Gln Asn Arg Lys Phe Leu Thr His His Glu Ile Asn Leu Leu Leu
 1               5                  10                  15

Gln Ser Val Lys Gln Lys Ser Cys Ser Ser Arg Asp Val Cys Met Ile
            20                  25                  30

Leu Leu Ala Tyr Phe His Gly Leu Arg Val Ser Glu Leu Leu Ser Leu
        35                  40                  45

Gln Leu Ser Asp Leu Glu Leu Thr Thr Glu Lys Ile Tyr Ile Gln Arg
    50                  55                  60

Ile Lys Asn Gly Phe Ser Thr Val His Pro Leu Gln Lys Glu Glu Val
65                  70                  75                  80

Ile Ala Ile Thr Asn Trp Leu Asn Glu Arg Asn Ser Leu Asn Val Lys
                85                  90                  95

His Phe Asn Asp Asn Pro Trp Leu Phe Val Ser Arg Thr Gly Lys Pro
            100                 105                 110

Leu Ser Arg Gln Arg Phe Tyr Asn Ile Val Ser Ala Ala Gly Lys Asn
        115                 120                 125

Ala Gly Leu Asn Ile Lys Val His Pro His Met Leu Arg His Ala Cys
    130                 135                 140

Gly Tyr Ser Leu Ala Asp Asn Gly Val Asp Thr Arg Leu Ile Gln Asp
145                 150                 155                 160

Tyr Leu Gly His Arg Asn Ile Arg His Thr Val Ile Tyr Thr Ala Ser
                165                 170                 175

Asn Ser Met Arg Phe Glu Lys Met Trp Gly Ile Gly Asp Ala Lys Lys
            180                 185                 190

Gln His Phe Asp Pro Lys Cys Lys Pro Asn Leu Cys Leu Glu Ile Leu
        195                 200                 205
```

Val

```
<210> SEQ ID NO 9
<211> LENGTH: 570
<212> TYPE: DNA
<213> ORGANISM: E. coli CFT073
<220> FEATURE:
<221> NAME/KEY: CDS
<222> LOCATION: (1)..(570)

<400> SEQUENCE: 9 atg cgc aaa ttt att act cat agt gaa tgg ttg tta ttt ttt gaa gcc      48
Met Arg Lys Phe Ile Thr His Ser Glu Trp Leu Leu Phe Phe Glu Ala
 1               5                  10                  15 atc aac ggt tca aaa aat gaa att aga gat aaa gcc atg tta caa atg      96
Ile Asn Gly Ser Lys Asn Glu Ile Arg Asp Lys Ala Met Leu Gln Met
             20                  25                  30 gca tat gta cat ggt ctt agg gta agc gag ctt att gca cta aag att     144
Ala Tyr Val His Gly Leu Arg Val Ser Glu Leu Ile Ala Leu Lys Ile
         35                  40                  45 agc gac att gac ttt tca gag tca gca ata tat atc aag cgt tta aaa     192
Ser Asp Ile Asp Phe Ser Glu Ser Ala Ile Tyr Ile Lys Arg Leu Lys
     50                  55                  60 aat gga tta tcc aca gta cat ccc ctg caa aaa gaa act gtt ctg tta     240
Asn Gly Leu Ser Thr Val His Pro Leu Gln Lys Glu Thr Val Leu Leu
 65                  70                  75                  80 tta aaa aaa tgg cta gca cta cgt gat aac ata gta aaa aaa cct ttt     288
Leu Lys Lys Trp Leu Ala Leu Arg Asp Asn Ile Val Lys Lys Pro Phe
                 85                  90                  95 gaa gac tct ttg ttt ctt tct tgt caa gga aat aaa atc tcg aga caa     336
Glu Asp Ser Leu Phe Leu Ser Cys Gln Gly Asn Lys Ile Ser Arg Gln
            100                 105                 110 tat gtg tat aag atg tgt aag aaa tat agt cac aat atg aat att aat     384
Tyr Val Tyr Lys Met Cys Lys Lys Tyr Ser His Asn Met Asn Ile Asn
        115                 120                 125 att cat cct cac atg ctt agg cat ggt tgt ggg tat gct tta gct aat     432
Ile His Pro His Met Leu Arg His Gly Cys Gly Tyr Ala Leu Ala Asn
    130                 135                 140 caa ggg tta gac acc aga cta ata caa gat tat tta ggg cac aga aat     480
Gln Gly Leu Asp Thr Arg Leu Ile Gln Asp Tyr Leu Gly His Arg Asn
145                 150                 155                 160 ata cat cat acg gta tta tat aca gcc agt aat gca gca aga ttt aaa     528
Ile His His Thr Val Leu Tyr Thr Ala Ser Asn Ala Ala Arg Phe Lys
                165                 170                 175 cga gta tgg gag ggt gat gtg tta gat ata aag aag ata taa             570
Arg Val Trp Glu Gly Asp Val Leu Asp Ile Lys Lys Ile
            180                 185                 190

<210> SEQ ID NO 10
<211> LENGTH: 189
<212> TYPE: PRT
<213> ORGANISM: E. coli CFT073

<400> SEQUENCE: 10

Met Arg Lys Phe Ile Thr His Ser Glu Trp Leu Leu Phe Phe Glu Ala
 1               5                  10                  15

Ile Asn Gly Ser Lys Asn Glu Ile Arg Asp Lys Ala Met Leu Gln Met
             20                  25                  30

Ala Tyr Val His Gly Leu Arg Val Ser Glu Leu Ile Ala Leu Lys Ile
         35                  40                  45

Ser Asp Ile Asp Phe Ser Glu Ser Ala Ile Tyr Ile Lys Arg Leu Lys
```

-continued

```
                50                      55                      60
Asn Gly Leu Ser Thr Val His Pro Leu Gln Lys Glu Thr Val Leu Leu
 65                      70                      75                      80

Leu Lys Lys Trp Leu Ala Leu Arg Asp Asn Ile Val Lys Lys Pro Phe
                 85                      90                      95

Glu Asp Ser Leu Phe Leu Ser Cys Gln Gly Asn Lys Ile Ser Arg Gln
            100                     105                     110

Tyr Val Tyr Lys Met Cys Lys Lys Tyr Ser His Asn Met Asn Ile Asn
            115                     120                     125

Ile His Pro His Met Leu Arg His Gly Cys Gly Tyr Ala Leu Ala Asn
        130                     135                     140

Gln Gly Leu Asp Thr Arg Leu Ile Gln Asp Tyr Leu Gly His Arg Asn
145                     150                     155                     160

Ile His His Thr Val Leu Tyr Thr Ala Ser Asn Ala Ala Arg Phe Lys
                165                     170                     175

Arg Val Trp Glu Gly Asp Val Leu Asp Ile Lys Lys Ile
            180                     185

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
ggagtggcga tgctgcgttg                                                    20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
cacaggggaa ggtgagatat gc                                                 22

<210> SEQ ID NO 13
<211> LENGTH: 6190
<212> TYPE: DNA
<213> ORGANISM: E. coli CFT073
<220> FEATURE:
<221> NAME/KEY: CDS
<222> LOCATION: (3507)..(4844)
<223> OTHER INFORMATION: permease
<220> FEATURE:
<221> NAME/KEY: CDS
<222> LOCATION: (4862)..(6190)
<223> OTHER INFORMATION: deaminase
<220> FEATURE:
<221> NAME/KEY: CDS
<222> LOCATION: (1378)..(1947)
<223> OTHER INFORMATION: dsdB fim B homolog

<400> SEQUENCE: 13
ctatacgaga atttctaaac aaagattggg tttacatttt gggtcaaaat gttgcttttt        60
tgcgtcacct atcccccaca ttttttcaaa tctcattgaa ttagaagcag tataaattac      120
cgtatgcctg atattcgat gcccgagata gtcctgaata agacgggtat ccacaccatt       180
atctgctagt gaataaccac atgcatggcg taacatatgt ggatgaactt taatatttaa     240
```

```
acctgcattt ttacccgcag cagaaactat gttataaaat cgttgtctcg ataatggttt      300
tcctgttcgg gaaacaaata accacgggtt atcattgaaa tgtttaacat ttaatgaatt      360
cctttcattc agccagtttg ttattgcaat caccctcttcc ttttgaagtg atggactgt      420 actgaatcca ttttttatcc gttgaatata tatttttct gtagttagtt ctaaatccga      480
caactgcaga gataagagct cactaacacg cagaccatga aaataagcca ataaaatcat      540
gcaaacatcg cgtgaagagc aactcttttg ttttacagat tgaagtagta aattaatttc      600
atgatgcgtt aaaattttc tgttttgcat aaatcacctc tatttatatg aaatagccat      660
gtcaactatg atgaaagaat tacatttagt caataatata attcatatag ttgctgtatg      720
attatagatt aatttattaa aattcaccta atctaattaa tcgcttgtaa acgcatataa      780
acaaccttcg ttatgtaact atcgttcaaa actctcttgt aaatataaag agccctataa      840
gatgattata aaaagtcct acaacccgaa atagcattcc ctcataaaat taagctcaac      900
atcggcatat ttaaaagta tccaatgcaa ttaatatttt atctaaaatt aacattgtat      960
cttgtatata ttcatccat gaatgtatgg atttttttat ttaaaaatta atgcactata     1020
acaaaaaaca tcaccaagtg ttaaaactaa cacaacaatt aaccaaaata atatggctgt     1080
ttatttttca tccgtaaaca aaaaggtaca aatattttca ccacaaaaaa accaccagca     1140
tggcattgaa ttaccattca caatacacac ctcctttcgc ttatttatgc tcattggttg     1200
actaataatg atctataccc cctgggcaac tatctctctg gcggggtatt gatgaatatc     1260
catttagtgg cataatttaa accccagctc attatttgct tataaaaaca agcaataata     1320
ccaggctctg gtatttatag ttcatttttt aacttaatta atataaccga taatatt       1377 atg cgc aaa ttt att act cat agt gaa tgg ttg tta ttt ttt gaa gcc     1425
Met Arg Lys Phe Ile Thr His Ser Glu Trp Leu Leu Phe Phe Glu Ala
  1               5                  10                  15 atc aac ggt tca aaa aat gaa att aga gat aaa gcc atg tta caa atg     1473
Ile Asn Gly Ser Lys Asn Glu Ile Arg Asp Lys Ala Met Leu Gln Met
         20                  25                  30 gca tat gta cat ggt ctt agg gta agc gag ctt att gca cta aag att     1521
Ala Tyr Val His Gly Leu Arg Val Ser Glu Leu Ile Ala Leu Lys Ile
     35                  40                  45 agc gac att gac ttt tca gag tca gca ata tat atc aag cgt tta aaa     1569
Ser Asp Ile Asp Phe Ser Glu Ser Ala Ile Tyr Ile Lys Arg Leu Lys
 50                  55                  60 aat gga tta tcc aca gta cat ccc ctg caa aaa gaa act gtt ctg tta     1617
Asn Gly Leu Ser Thr Val His Pro Leu Gln Lys Glu Thr Val Leu Leu
 65                  70                  75                  80 tta aaa aaa tgg cta gca cta cgt gat aac ata gta aaa aaa cct ttt     1665
Leu Lys Lys Trp Leu Ala Leu Arg Asp Asn Ile Val Lys Lys Pro Phe
                 85                  90                  95 gaa gac tct ttg ttt ctt tct tgt caa gga aat aaa atc tcg aga caa     1713
Glu Asp Ser Leu Phe Leu Ser Cys Gln Gly Asn Lys Ile Ser Arg Gln
            100                 105                 110 tat gtg tat aag atg tgt aag aaa tat agt cac aat atg aat att aat     1761
Tyr Val Tyr Lys Met Cys Lys Lys Tyr Ser His Asn Met Asn Ile Asn
        115                 120                 125 att cat cct cac atg ctt agg cat ggt tgt ggg tat gct tta gct aat     1809
Ile His Pro His Met Leu Arg His Gly Cys Gly Tyr Ala Leu Ala Asn
    130                 135                 140 caa ggg tta gac acc aga cta ata caa gat tat tta ggg cac aga aat     1857
Gln Gly Leu Asp Thr Arg Leu Ile Gln Asp Tyr Leu Gly His Arg Asn
145                 150                 155                 160
```

```
ata cat cat acg gta tta tat aca gcc agt aat gca gca aga ttt aaa      1905
Ile His His Thr Val Leu Tyr Thr Ala Ser Asn Ala Ala Arg Phe Lys
                165                 170                 175 cga gta tgg gag ggt gat gtg tta gat ata aag aag ata taa              1947
Arg Val Trp Glu Gly Asp Val Leu Asp Ile Lys Lys Ile
            180                 185                 190 cccctgttct aaaggcctca attcattgag cttttagcc cctcattttt atgacataca     2007
actgataatc ataatggatc tcaatattaa tcaaaatgag aaataaatca ccttttatt     2067 aaaaaattaa ttttttaaa gtcacaaacc aacacatata atatttaata aaaatgccac     2127
cagcaaatat attgccactt atcttttctc tggtaatcta gtttactata aattatcgct    2187
ctccaatatt cgacgccaag aagaagtggt tattttattt atccttttcg taactattga    2247
caaaacaatt cccatataaa aattgcaatt tataaagcca acatacactt acagtgcata    2307
ataaggttat ttaggaacca gatgatttaa tgtattataa ggtataacat tcatattgac    2367
ttacctgttc tcttaaccaa gtaataaatg cctcaatttt tggccactgc ctgcccgta     2427 atgtggtgat gtaataatgc tgatggcatt tcaccgtcat atcgccaaac ggcgcgacga    2487
gctcaccact ggcaagcctt ttttgtacca tacgttcct tcccatcgcc accccaatat     2547
gattcatcgc ggcgataacg gctaaatcag agcgatcaaa gccaattcca aagatgttg     2607 gcaaattaac cgcataatgt tgcgcccaac tatgccattc atccgtaccg gagtcgttgc    2667
tccatgcctg tctgtcatgg agcaacgtac agtgacgcag gttaattacc gtgttggtta   2727
aatcatgtct ttgagcgtac tccgggctgc aaactggcaa gatttcttca tccatcagaa    2787
agtgatgagc caattgcgct gacggcgcat catcaaagta gatcgccaaa tcgattccgg    2847
cacgttgcaa attgacattg tcattaccag tgagcacggt gagcgaaata gacggatatc    2907
ggcgtgtaaa gtcacctaat gcgggcacca accagcattg ggcgatagag ggccgggaat    2967
acagcgttaa cgttcccgat aactcctgat ttttgatatc cagaatttcc tgattcaggg    3027
tatccagcga cgattttagc gcccaataaa cacgtttccc ctcgtgcgtt aattccactt    3087
tgcgatggga acgaacaaac aactgaatac ctaattcttc ttccagctga ttgatacggt   3147
gacttaccgc actggggctc agcgacaatt cctctgccgc gagagcgaag gactgatgcc    3207
tggcagccac ttcaaaagta tgcagttttg atagttgcca gccgttaagc agtcgatttc    3267
ttatttcacg aaggggttcc ataatcacct cattttctc ttaagtgtaa aaaaatagcg     3327
gcaaaatttc agctgtaagg tgagctaaag tgaaccatat ctcaattcac cttcattttt    3387
agatgtaaat cactcccttg atgcaattta gctcatgtga aaggcaaatt ttatcgtttg    3447
tcagcctgcg ttgttttttt gtccaatatc atcaggttaa tcacagggga aggtgagat     3506 atg cac tct caa atc tgg gtt gtg agc acg ctg ctt atc agc atc gtg      3554
Met His Ser Gln Ile Trp Val Val Ser Thr Leu Leu Ile Ser Ile Val
                195                 200                 205 tta att gta ctg acc atc gtg aag ttc aaa ttc cac ccg ttt ctg gcg      3602
Leu Ile Val Leu Thr Ile Val Lys Phe Lys Phe His Pro Phe Leu Ala
            210                 215                 220 ctg ttg ctg gcc agc ttc ttc gtg gga acg atg atg ggc atg ggg cca      3650
Leu Leu Leu Ala Ser Phe Phe Val Gly Thr Met Met Gly Met Gly Pro
        225                 230                 235 ctg gat atg gta aat gct att gaa agt gga att ggc gga acg ctg ggg      3698
Leu Asp Met Val Asn Ala Ile Glu Ser Gly Ile Gly Gly Thr Leu Gly
        240                 245                 250 ttc ctc gct gcg gtt atc ggc ctt ggc acg ata ctg gga aaa atg atg      3746
Phe Leu Ala Ala Val Ile Gly Leu Gly Thr Ile Leu Gly Lys Met Met
255                 260                 265                 270
```

```
gaa gta tcc ggg gcc gca gaa aga att ggt ctg aca ctt caa cgc tgc    3794
Glu Val Ser Gly Ala Ala Glu Arg Ile Gly Leu Thr Leu Gln Arg Cys
                275                 280                 285 cgg tgg ctt tca gct gat gtc att atg gtg ctg gtt ggc ctg att tgc    3842
Arg Trp Leu Ser Ala Asp Val Ile Met Val Leu Val Gly Leu Ile Cys
        290                 295                 300 ggc atc acg ctg ttt gtt gaa gtg ggc gtc gtg cta ttg att cct ctg    3890
Gly Ile Thr Leu Phe Val Glu Val Gly Val Val Leu Leu Ile Pro Leu
            305                 310                 315 gct ttt tca att gcc aaa aaa acc aat acc tca ttg tta aag ctg gcc    3938
Ala Phe Ser Ile Ala Lys Lys Thr Asn Thr Ser Leu Leu Lys Leu Ala
        320                 325                 330 att ccg ctg tgt acc gca ttg atg gca gtg cac tgc gtg gtt ccc cca    3986
Ile Pro Leu Cys Thr Ala Leu Met Ala Val His Cys Val Val Pro Pro
335                 340                 345                 350 cat ccg gct gct tta tat gtt gcc aat aag ctg ggc gca gat atc ggt    4034
His Pro Ala Ala Leu Tyr Val Ala Asn Lys Leu Gly Ala Asp Ile Gly
                355                 360                 365 tcg gtg atc gtc tac ggt ttg ctg gtt ggg ctg atg gca tca ctg atc    4082
Ser Val Ile Val Tyr Gly Leu Leu Val Gly Leu Met Ala Ser Leu Ile
            370                 375                 380 ggt ggc cca ctt ttc ctt aaa ttt ctg ggt caa cga ctg ccc ttt aaa    4130
Gly Gly Pro Leu Phe Leu Lys Phe Leu Gly Gln Arg Leu Pro Phe Lys
        385                 390                 395 cct gta ccc aca gag ttt gcc gat ctc aaa gtt cgc gat gaa aaa aca    4178
Pro Val Pro Thr Glu Phe Ala Asp Leu Lys Val Arg Asp Glu Lys Thr
400                 405                 410 cta ccg tca tta ggc gca acg tta ttc acc gta ctg cta ccc att gcg    4226
Leu Pro Ser Leu Gly Ala Thr Leu Phe Thr Val Leu Leu Pro Ile Ala
415                 420                 425                 430 ctg atg ttg gtt aaa acg att gcc gaa ttg aat atg gca cgt gag agt    4274
Leu Met Leu Val Lys Thr Ile Ala Glu Leu Asn Met Ala Arg Glu Ser
                435                 440                 445 ggt ttg tat acc ttg ctt gag ttt att ggc aac cct atc act gcc acg    4322
Gly Leu Tyr Thr Leu Leu Glu Phe Ile Gly Asn Pro Ile Thr Ala Thr
            450                 455                 460 ttt atc gcc gtg ttt gtc gcc tat tat gtg ttg ggt ata cgt cag cat    4370
Phe Ile Ala Val Phe Val Ala Tyr Tyr Val Leu Gly Ile Arg Gln His
        465                 470                 475 atg agc atg ggg acg atg ctc aca cat acg gaa aat ggt ttc ggt tct    4418
Met Ser Met Gly Thr Met Leu Thr His Thr Glu Asn Gly Phe Gly Ser
480                 485                 490 att gct aat att ttg ctg att atc ggg gcc gga ggc gca ttc aac gcc    4466
Ile Ala Asn Ile Leu Leu Ile Ile Gly Ala Gly Gly Ala Phe Asn Ala
495                 500                 505                 510 att tta aaa agc agc agt ctc gct gat acg ctg gca gtt att ctc tcc    4514
Ile Leu Lys Ser Ser Ser Leu Ala Asp Thr Leu Ala Val Ile Leu Ser
                515                 520                 525 aat atg cat atg cac ccg att ctt ctg gcc tgg ttg gtg gca ctt att    4562
Asn Met His Met His Pro Ile Leu Leu Ala Trp Leu Val Ala Leu Ile
            530                 535                 540 ctg cat gct gca gtg ggc tcc gct acg gtg gca atg atg ggg gca acg    4610
Leu His Ala Ala Val Gly Ser Ala Thr Val Ala Met Met Gly Ala Thr
        545                 550                 555 gca att gtt gca ccc atg ctg ccg ctg tat ccc gac atc agc ccg gaa    4658
Ala Ile Val Ala Pro Met Leu Pro Leu Tyr Pro Asp Ile Ser Pro Glu
560                 565                 570 att att gcg att gct atc ggt tcc ggt gcg att ggc tgc acg atc gtt    4706
Ile Ile Ala Ile Ala Ile Gly Ser Gly Ala Ile Gly Cys Thr Ile Val
```

```
                575                 580                 585                 590
acg gac tca ctt ttc tgg ctg gtg aag caa tat tgc ggc gct acg ctc         4754
Thr Asp Ser Leu Phe Trp Leu Val Lys Gln Tyr Cys Gly Ala Thr Leu
                595                 600                 605 aat gaa aca ttt aaa tac tat acg aca gcg aca ttt atc gct tca gtc         4802
Asn Glu Thr Phe Lys Tyr Tyr Thr Thr Ala Thr Phe Ile Ala Ser Val
            610                 615                 620 atc gct ctg gcg ggc aca ttc ctg ctg tca ttt atc atc taa                  4844
Ile Ala Leu Ala Gly Thr Phe Leu Leu Ser Phe Ile Ile
            625                 630                 635 gcgcaaagag acgtact atg gaa aac gct aaa atg aat tcg ctc atc gcc          4894
                   Met Glu Asn Ala Lys Met Asn Ser Leu Ile Ala
                                640                 645 cag tat ccg ttg gta gag gat ctg gtt gct ctt aaa gaa acc acc tgg         4942
Gln Tyr Pro Leu Val Glu Asp Leu Val Ala Leu Lys Glu Thr Thr Trp
            650                 655                 660 ttt aat cct ggc acg acc tca ttg gca gaa ggt tta cct tat gtt ggc         4990
Phe Asn Pro Gly Thr Thr Ser Leu Ala Glu Gly Leu Pro Tyr Val Gly
        665                 670                 675 ctg acc gaa cag gat gtt cag gac gcc cat gcg cgc ctg tct cgt ttt         5038
Leu Thr Glu Gln Asp Val Gln Asp Ala His Ala Arg Leu Ser Arg Phe
680                 685                 690                 695 gcg ccg tat ctg gca aaa gca ttt cct gaa acg gct gcc gcg ggg ggg         5086
Ala Pro Tyr Leu Ala Lys Ala Phe Pro Glu Thr Ala Ala Ala Gly Gly
                700                 705                 710 att att gaa tca gaa ctg gtt gct att cct gct atg caa aaa cgg ctg         5134
Ile Ile Glu Ser Glu Leu Val Ala Ile Pro Ala Met Gln Lys Arg Leu
                715                 720                 725 gaa aag gaa tat caa caa ccg atc gcc ggg caa ttg cta cta aaa aaa         5182
Glu Lys Glu Tyr Gln Gln Pro Ile Ala Gly Gln Leu Leu Leu Lys Lys
            730                 735                 740 gac agc cat ttg ccg att tcc ggc tcc ata aaa gca cgt ggc ggg att         5230
Asp Ser His Leu Pro Ile Ser Gly Ser Ile Lys Ala Arg Gly Gly Ile
        745                 750                 755 tat gaa gtc ctg gcc cat gct gaa aaa ctg gct ctg gaa gcg ggt ttg         5278
Tyr Glu Val Leu Ala His Ala Glu Lys Leu Ala Leu Glu Ala Gly Leu
760                 765                 770                 775 ctg aca ctt gag gat gat tac agc aaa ctg ctt tcc ccg gag ttt aaa         5326
Leu Thr Leu Glu Asp Asp Tyr Ser Lys Leu Leu Ser Pro Glu Phe Lys
                780                 785                 790 cag ttc ttt agc caa tac agt att gct gtg gga tca acc gga aat ctg         5374
Gln Phe Phe Ser Gln Tyr Ser Ile Ala Val Gly Ser Thr Gly Asn Leu
            795                 800                 805 ggg tta tca att ggt att atg agc gcc cgc atc ggc ttt aaa gta acg         5422
Gly Leu Ser Ile Gly Ile Met Ser Ala Arg Ile Gly Phe Lys Val Thr
        810                 815                 820 gtg cat atg tct gct gat gcc cgc gcc tgg aaa aaa gcg aaa ctg cgc         5470
Val His Met Ser Ala Asp Ala Arg Ala Trp Lys Lys Ala Lys Leu Arg
825                 830                 835 agt cat ggc gtt act gtc gtg gaa tac gag caa gat tat ggt gtt gcc         5518
Ser His Gly Val Thr Val Val Glu Tyr Glu Gln Asp Tyr Gly Val Ala
840                 845                 850                 855 gtc gag gaa gga cgt aaa gcc gcg cag tct gac ccg aac tgt ttc ttt         5566
Val Glu Glu Gly Arg Lys Ala Ala Gln Ser Asp Pro Asn Cys Phe Phe
                860                 865                 870 att gat gac gaa aat tcc cgc acg ttg ttc ctt gga tat tcc gtc gca         5614
Ile Asp Asp Glu Asn Ser Arg Thr Leu Phe Leu Gly Tyr Ser Val Ala
            875                 880                 885 ggc cag cgt ctt aag gcg caa ttt gct cag caa ggt cgc atc gtc gat         5662
```

```
                Gly Gln Arg Leu Lys Ala Gln Phe Ala Gln Gln Gly Arg Ile Val Asp
                        890                 895                 900 gct gat aac cct ctg ttt gtc tat ctg ccg tgt ggt gtt ggc ggt ggt           5710
Ala Asp Asn Pro Leu Phe Val Tyr Leu Pro Cys Gly Val Gly Gly Gly
        905                 910                 915 cct ggt ggc gtc gca ttc gga ctt aaa ctg gcg ttt ggc gat cat gtt          5758
Pro Gly Gly Val Ala Phe Gly Leu Lys Leu Ala Phe Gly Asp His Val
920                 925                 930                 935 cac tgc ttt ttt gcc gaa cca aca cac tcc ccg tgt atg tta tta ggc          5806
His Cys Phe Phe Ala Glu Pro Thr His Ser Pro Cys Met Leu Leu Gly
                940                 945                 950 gtc cat acc gga tta cac gat cag att tct gtt cag gat att ggc atc          5854
Val His Thr Gly Leu His Asp Gln Ile Ser Val Gln Asp Ile Gly Ile
            955                 960                 965 gac aac ctt acc gct gcc gat ggc ctt gca gtt ggt cgc gca tcg ggc          5902
Asp Asn Leu Thr Ala Ala Asp Gly Leu Ala Val Gly Arg Ala Ser Gly
        970                 975                 980 ttt gtc ggg cgg gca atg gag cgt ctg ctg gat ggt ttc tat acc ctt          5950
Phe Val Gly Arg Ala Met Glu Arg Leu Leu Asp Gly Phe Tyr Thr Leu
    985                 990                 995 agc gat caa acc atg tat gac atg ctt ggc tgg ctg gcg cag gaa gaa          5998
Ser Asp Gln Thr Met Tyr Asp Met Leu Gly Trp Leu Ala Gln Glu Glu
1000                1005                1010                1015 ggt att cgt ctt gaa cca tcg gca ctg gcg ggt atg gcc ggg tct cag          6046
Gly Ile Arg Leu Glu Pro Ser Ala Leu Ala Gly Met Ala Gly Ser Gln
            1020                1025                1030 cgc gtg tgc gca tca gta agt tac caa cag atg cac ggt ttc agc gcc          6094
Arg Val Cys Ala Ser Val Ser Tyr Gln Gln Met His Gly Phe Ser Ala
        1035                1040                1045 gaa caa ctg cgt aat gcc act cat ctg gtg tgg gcg acg gga ggt gga          6142
Glu Gln Leu Arg Asn Ala Thr His Leu Val Trp Ala Thr Gly Gly Gly
    1050                1055                1060 atg gtg ccg gaa gaa gag atg aat caa tat ctg gca aaa ggc cgt taa          6190
Met Val Pro Glu Glu Glu Met Asn Gln Tyr Leu Ala Lys Gly Arg
1065                1070                1075

<210> SEQ ID NO 14
<211> LENGTH: 189
<212> TYPE: PRT
<213> ORGANISM: E. coli CFT073

<400> SEQUENCE: 14

Met Arg Lys Phe Ile Thr His Ser Glu Trp Leu Leu Phe Phe Glu Ala
1               5                   10                  15

Ile Asn Gly Ser Lys Asn Glu Ile Arg Asp Lys Ala Met Leu Gln Met
            20                  25                  30

Ala Tyr Val His Gly Leu Arg Val Ser Glu Leu Ile Ala Leu Lys Ile
        35                  40                  45

Ser Asp Ile Asp Phe Ser Glu Ser Ala Ile Tyr Ile Lys Arg Leu Lys
    50                  55                  60

Asn Gly Leu Ser Thr Val His Pro Leu Gln Lys Glu Thr Val Leu Leu
65                  70                  75                  80

Leu Lys Lys Trp Leu Ala Leu Arg Asp Asn Ile Val Lys Lys Pro Phe
                85                  90                  95

Glu Asp Ser Leu Phe Leu Ser Cys Gln Gly Asn Lys Ile Ser Arg Gln
            100                 105                 110

Tyr Val Tyr Lys Met Cys Lys Lys Tyr Ser His Asn Met Asn Ile Asn
        115                 120                 125
```

```
Ile His Pro His Met Leu Arg His Gly Cys Gly Tyr Ala Leu Ala Asn
    130                 135                 140

Gln Gly Leu Asp Thr Arg Leu Ile Gln Asp Tyr Leu Gly His Arg Asn
145                 150                 155                 160

Ile His His Thr Val Leu Tyr Thr Ala Ser Asn Ala Ala Arg Phe Lys
                165                 170                 175

Arg Val Trp Glu Gly Asp Val Leu Asp Ile Lys Lys Ile
            180                 185

<210> SEQ ID NO 15
<211> LENGTH: 445
<212> TYPE: PRT
<213> ORGANISM: E. coli CFT073

<400> SEQUENCE: 15

Met His Ser Gln Ile Trp Val Val Ser Thr Leu Leu Ile Ser Ile Val
  1               5                  10                  15

Leu Ile Val Leu Thr Ile Val Lys Phe Lys Phe His Pro Phe Leu Ala
                 20                  25                  30

Leu Leu Leu Ala Ser Phe Phe Val Gly Thr Met Met Gly Met Gly Pro
             35                  40                  45

Leu Asp Met Val Asn Ala Ile Glu Ser Gly Ile Gly Gly Thr Leu Gly
         50                  55                  60

Phe Leu Ala Ala Val Ile Gly Leu Gly Thr Ile Leu Gly Lys Met Met
 65                  70                  75                  80

Glu Val Ser Gly Ala Ala Glu Arg Ile Gly Leu Thr Leu Gln Arg Cys
                 85                  90                  95

Arg Trp Leu Ser Ala Asp Val Ile Met Val Leu Val Gly Leu Ile Cys
                100                 105                 110

Gly Ile Thr Leu Phe Val Glu Val Gly Val Val Leu Leu Ile Pro Leu
            115                 120                 125

Ala Phe Ser Ile Ala Lys Lys Thr Asn Thr Ser Leu Leu Lys Leu Ala
        130                 135                 140

Ile Pro Leu Cys Thr Ala Leu Met Ala Val His Cys Val Val Pro Pro
145                 150                 155                 160

His Pro Ala Ala Leu Tyr Val Ala Asn Lys Leu Gly Ala Asp Ile Gly
                165                 170                 175

Ser Val Ile Val Tyr Gly Leu Leu Val Gly Leu Met Ala Ser Leu Ile
                180                 185                 190

Gly Gly Pro Leu Phe Leu Lys Phe Leu Gly Gln Arg Leu Pro Phe Lys
            195                 200                 205

Pro Val Pro Thr Glu Phe Ala Asp Leu Lys Val Arg Asp Glu Lys Thr
        210                 215                 220

Leu Pro Ser Leu Gly Ala Thr Leu Phe Thr Val Leu Leu Pro Ile Ala
225                 230                 235                 240

Leu Met Leu Val Lys Thr Ile Ala Glu Leu Asn Met Ala Arg Glu Ser
                245                 250                 255

Gly Leu Tyr Thr Leu Leu Glu Phe Ile Gly Asn Pro Ile Thr Ala Thr
                260                 265                 270

Phe Ile Ala Val Phe Val Ala Tyr Tyr Val Leu Gly Ile Arg Gln His
            275                 280                 285

Met Ser Met Gly Thr Met Leu Thr His Thr Glu Asn Gly Phe Gly Ser
        290                 295                 300

Ile Ala Asn Ile Leu Leu Ile Ile Gly Ala Gly Gly Ala Phe Asn Ala
305                 310                 315                 320
```

-continued

Ile Leu Lys Ser Ser Ser Leu Ala Asp Thr Leu Ala Val Ile Leu Ser
                325                 330                 335

Asn Met His Met His Pro Ile Leu Leu Ala Trp Leu Val Ala Leu Ile
            340                 345                 350

Leu His Ala Ala Val Gly Ser Ala Thr Val Ala Met Met Gly Ala Thr
        355                 360                 365

Ala Ile Val Ala Pro Met Leu Pro Leu Tyr Pro Asp Ile Ser Pro Glu
    370                 375                 380

Ile Ile Ala Ile Ala Ile Gly Ser Gly Ala Ile Gly Cys Thr Ile Val
385                 390                 395                 400

Thr Asp Ser Leu Phe Trp Leu Val Lys Gln Tyr Cys Gly Ala Thr Leu
                405                 410                 415

Asn Glu Thr Phe Lys Tyr Tyr Thr Thr Ala Thr Phe Ile Ala Ser Val
            420                 425                 430

Ile Ala Leu Ala Gly Thr Phe Leu Leu Ser Phe Ile Ile
        435                 440                 445

<210> SEQ ID NO 16
<211> LENGTH: 442
<212> TYPE: PRT
<213> ORGANISM: E. coli CFT073

<400> SEQUENCE: 16

Met Glu Asn Ala Lys Met Asn Ser Leu Ile Ala Gln Tyr Pro Leu Val
1               5                   10                  15

Glu Asp Leu Val Ala Leu Lys Glu Thr Thr Trp Phe Asn Pro Gly Thr
            20                  25                  30

Thr Ser Leu Ala Glu Gly Leu Pro Tyr Val Gly Leu Thr Glu Gln Asp
        35                  40                  45

Val Gln Asp Ala His Ala Arg Leu Ser Arg Phe Ala Pro Tyr Leu Ala
    50                  55                  60

Lys Ala Phe Pro Glu Thr Ala Ala Gly Gly Ile Ile Glu Ser Glu
65                  70                  75                  80

Leu Val Ala Ile Pro Ala Met Gln Lys Arg Leu Glu Lys Glu Tyr Gln
                85                  90                  95

Gln Pro Ile Ala Gly Gln Leu Leu Leu Lys Lys Asp Ser His Leu Pro
            100                 105                 110

Ile Ser Gly Ser Ile Lys Ala Arg Gly Gly Ile Tyr Glu Val Leu Ala
        115                 120                 125

His Ala Glu Lys Leu Ala Leu Glu Ala Gly Leu Leu Thr Leu Glu Asp
    130                 135                 140

Asp Tyr Ser Lys Leu Leu Ser Pro Glu Phe Lys Gln Phe Phe Ser Gln
145                 150                 155                 160

Tyr Ser Ile Ala Val Gly Ser Thr Gly Asn Leu Gly Leu Ser Ile Gly
                165                 170                 175

Ile Met Ser Ala Arg Ile Gly Phe Lys Val Thr Val His Met Ser Ala
            180                 185                 190

Asp Ala Arg Ala Trp Lys Lys Ala Lys Leu Arg Ser His Gly Val Thr
        195                 200                 205

Val Val Glu Tyr Glu Gln Asp Tyr Gly Val Ala Val Glu Glu Gly Arg
    210                 215                 220

Lys Ala Ala Gln Ser Asp Pro Asn Cys Phe Phe Ile Asp Asp Glu Asn
225                 230                 235                 240

Ser Arg Thr Leu Phe Leu Gly Tyr Ser Val Ala Gly Gln Arg Leu Lys

```
                    245                 250                 255
Ala Gln Phe Ala Gln Gln Gly Arg Ile Val Asp Ala Asp Asn Pro Leu
                260                 265                 270

Phe Val Tyr Leu Pro Cys Gly Val Gly Gly Pro Gly Gly Val Ala
            275                 280                 285

Phe Gly Leu Lys Leu Ala Phe Gly Asp His Val His Cys Phe Phe Ala
            290                 295                 300

Glu Pro Thr His Ser Pro Cys Met Leu Leu Gly Val His Thr Gly Leu
305                 310                 315                 320

His Asp Gln Ile Ser Val Gln Asp Ile Gly Ile Asp Asn Leu Thr Ala
                325                 330                 335

Ala Asp Gly Leu Ala Val Gly Arg Ala Ser Gly Phe Val Gly Arg Ala
            340                 345                 350

Met Glu Arg Leu Leu Asp Gly Phe Tyr Thr Leu Ser Asp Gln Thr Met
            355                 360                 365

Tyr Asp Met Leu Gly Trp Leu Ala Gln Glu Gly Ile Arg Leu Glu
        370                 375                 380

Pro Ser Ala Leu Ala Gly Met Ala Gly Ser Gln Arg Val Cys Ala Ser
385                 390                 395                 400

Val Ser Tyr Gln Gln Met His Gly Phe Ser Ala Glu Gln Leu Arg Asn
                405                 410                 415

Ala Thr His Leu Val Trp Ala Thr Gly Gly Met Val Pro Glu Glu
            420                 425                 430

Glu Met Asn Gln Tyr Leu Ala Lys Gly Arg
            435                 440

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 17
gcgctgcagc gttattaacg gccttttgcc agatattgat tc                          42

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 18
cgcggatccc gtactatgga aaacgctaaa atgaattcgc                             40
```

UROPATHOGENIC E. COLI D-SERINE DETOXIFICATION OPERON

CROSS-REFERENCE TO RELATED APPLICATIONS

This application is a divisional of U.S. patent application Ser. No. 10/117,417, filed Apr. 5, 2002, which claims priority to U.S. Provisional Application Ser. No. 60/281,859, filed Apr. 5, 2001, which is incorporated herein in its entirety.

STATEMENT REGARDING FEDERALLY SPONSORED RESEARCH OR DEVELOPMENT

This invention was made with United States government support awarded by the following agencies: NIH AI39000. The United States has certain rights in this invention.

BACKGROUND OF THE INVENTION

Urinary tract infections (UTIs) are responsible for an estimated 10 million outpatient visits and more than one million hospitalizations each year in the United States. Annual health care costs attributable to UTIs exceed one billion dollars. Approximately 50% of women will have at least one UTI during their lives, and many of these women experience recurrent UTI.

Uropathogenic *Eschericia coli* (UPEC), by far the most common uropathogen, is the causal agent in greater than 85% of uncomplicated UTIs. The organisms are also known to cause hospital acquired infections associated with injury, surgical procedures, or catheterization. UPEC present a complex ecological case among the pathogenic *E. coli*. UPEC can colonize the human intestinal tract without causing disease, yet they can sequentially colonize the perineum, urethra, bladder and kidney. Known *E. coli* virulence factors that contribute to UTIs are fimbriae (e.g. type 1 fimbriae and Pap fimbriae), iron acquisition systems, hemolysin, cytotoxic necrotizing factor-1, and the Sat autotransporter. Environmental cues used by UPEC for expression of genes needed for colonization of the bladder and kidney have not been described in the literature.

Urinary tract infections in humans are generally treated with antibiotic therapy. Treatment of UTIs may be complicated by strains that are resistant to antibiotics, particularly to those antibiotics in common use. The identification of new UPEC-specified pathogenicity factors will facilitate the development of new methods of treating or preventing UTIs.

BRIEF SUMMARY OF THE INVENTION

In one aspect, the present invention provides a method of detecting uropathogenic *E. coli* nucleotide sequences differentially expressed in the presence or absence of D-serine comprising providing a library comprising a plurality of transposon mutants of a uropathogenic *E. coli* strain, the mutants comprising a transcriptional fusion comprising a transcriptional regulation sequence operably connected to a sequence encoding a detectable protein; growing the mutants in the presence or absence of D-serine; identifying mutants having increased or decreased expression of the transcriptional fusion in the presence or absence of D-serine by comparing the relative levels of the detectable protein of the mutants grown in the presence or absence of D-serine; identifying the insertion site of the transcriptional fusion in the identified transposon mutants; and correlating the insertion site with an *E. coli* nucleotide sequence.

In another aspect, the present invention provides a method of identifying proteins differentially expressed in a wild-type uropathogenic *E. coli* strain and a uropathogenic *E. coli* dsdCXA locus mutant, the mutant having reduced expression of one or more proteins selected from the group consisting of DsdA, DsdC, and DsdX, the method comprising comparing proteins isolated from the wild-type uropathogenic *E. coli* strain and proteins isolated from the uropathogenic *E. coli* dsdCXA locus mutant; and identifying proteins from the dsdCXA mutant having increased or decreased level of expression relative to expression of the corresponding proteins in the wild-type uropathogenic *E. coli* strain.

In other aspects, the invention includes a method of identifying a uropathogenic *E. coli* polynucleotide sequence that binds to DsdC protein comprising contacting an *E. coli* polynucleotide sequence with DsdC protein and detecting binding of the polynucleotide sequence to the protein.

In another aspect, the present invention provides a method of detecting genes from a uropathogenic *E. coli* strain that are differentially expressed in the presence or absence of D-serine comprising hybridizing a first set of labeled oligonucleotide probes with an array of oligomers, the oligomers comprising gene sequences from the uropathogenic *E. coli* strain, wherein the first set of labeled oligonucleotide probes is made by reverse transcription of RNA isolated from uropathogenic *E. coli* grown in the presence of D-serine; hybridizing a second set of labeled oligonucleotide probes with an array of oligomers identical to the aforementioned array, wherein the second set of labeled oligonucleotide probes is made by reverse transcription of RNA isolated from uropathogenic *E. coli* grown in the absence of D-serine; comparing hybridization of labeled oligonucleotide probes to identify oligomers having differential hybridization to the first and second sets of oligonucleotide probes; and identifying genes comprising the sequences of the identified oligomers.

In yet another aspect, the present invention provides a method of detecting proteins differentially expressed in a uropathogenic *E. coli* strain in response to D-serine, comprising providing a first culture of the uropathogenic *E. coli* strain grown in the presence of D-serine and a second culture of the uropathogenic *E. coli* strain grown in the absence of D-serine; comparing proteins isolated from the two cultures, and identifying proteins from *E. coli* grown in the presence of D-serine that are increased or decreased relative to the corresponding proteins in the uropathogenic *E. coli* strain grown in the absence of D-serine.

The present invention also provides a method of characterizing bacterial strains isolated from clinical samples comprising testing the strain for the ability to grow in the presence of D-serine.

In another aspect, the present invention provides urine dipstick comprising a solid support, a polypeptide comprising D-serine deaminase and an indicator responsive to ammonia, wherein the polypeptide and indicator are coimmobilized on the support.

DETAILED DESCRIPTION OF THE INVENTION

Figure 1:
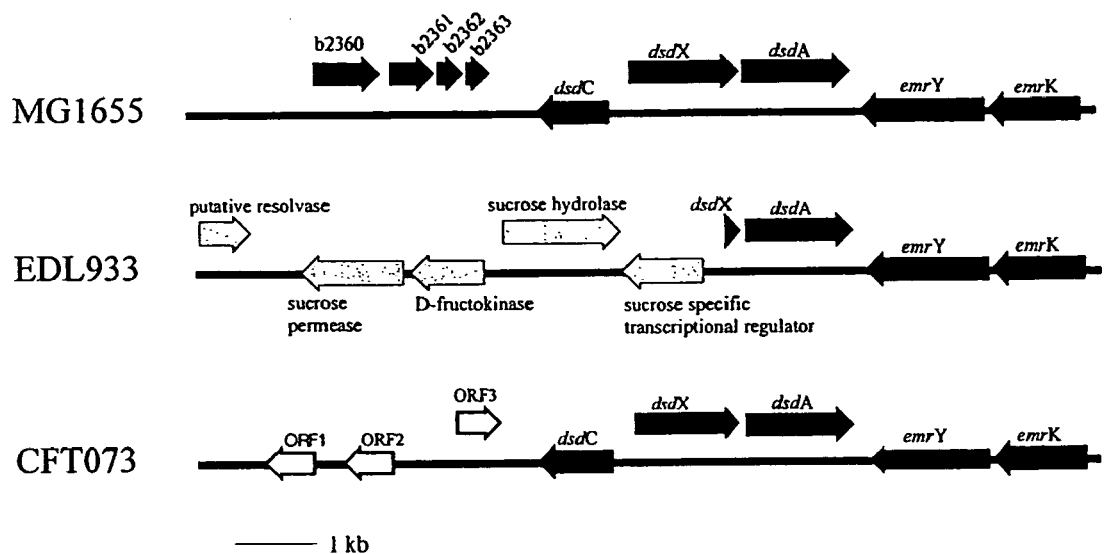
FIG. 1 compares the 53 minute regions of three *E. coli* strains: laboratory K-12 strain MG1655, enterohemorhagic *E. coli* (EHEC) EDL933, and uropathogenic *E. coli* CFT073.

The sequence of the uropathogenic *E. coli* strain CFT073 genome was compared with the sequences of the genomes of *E. coli* laboratory K-12 strain MG1655 and enterohemorrhagic *E. coli* (EHEC) 0157 strain EDL933. A sequence found in uropathogenic *E. coli* strain CFT073 but not in *E. coli* K-12 or EHEC 0157 was identified in the 53 minute region of the K-12 genetic map. The sequence includes the D-serine tolerance (dsdCXA) locus, which is involved in overcoming D-serine toxicity, and is presented in SEQ ID NO:13.

The dsd locus includes coding sequences for a positive transcriptional activator (DsdC), a putative permease (DsdX), and a D-serine deaminase (DsdA), which catalyzes the hydrolysis of D-serine to give pyruvate and ammonia. The 53 minute region includes two putative recombinases unique to UPEC, which are designated ipuA and ipuB. The DNA sequences of dsdC, dsdX dsdA, ipuA and ipuB are provided in SEQ ID NO:1, SEQ ID NO:3, SEQ ID NO:5, SEQ ID NO:7, and SEQ ID NO:9, respectively, and the deduced amino acid sequences of their putative translation products are shown in SEQ ID NO:2, SEQ ID NO:4, SEQ ID NO:6, SEQ ID NO:8, and SEQ ID NO:10, respectively. With reference to the SEQ ID NO:13, bases 3507-4844 correspond to SEQ ID NO:3; bases 4862-6190 correspond to SEQ ID NO:5; bases 1378-1947 correspond to SEQ ID NO:9; bases 3295-2342 correspond to the reverse complement of SEQ ID NO:1; and bases 623-7 correspond to the reverse complement of SEQ ID NO:7.

Based on their deduced amino acid sequences, the proteins putatively encoded by ipuA and ipuB are homologs of the recombinase fimB, which suggests that the proteins may function to regulate expression of the dsd operon in a manner similar to the regulation of type 1 fimbriae by FimB and FimE.

The polypeptide putatively encoded by dsdC is a member of the LysR family of transcriptional regulators. The LysR-type regulators are very common in bacteria and control the expression of genes associated with a wide range of cellular processes, including many diverse virulence factors. Members of the LysR family of transcriptional regulators usually require the presence of a specific coinducer to activate transcription. The polypeptides are about 270-330 amino acid residues in length and exhibit sequence similarity over about 270 amino acid residues. The strongest conservation occurs in the N-terminal 66 amino acid residues, which has a helix-turn-helix motif. The LysR-type regulators bind to DNA as dimers or tetramers and activate gene transcription, possibly by introducing a bend in the DNA helix.

Until recently, it was considered axiomatic that naturally occurring D-amino acids occurred only in bacteria, which contain D-amino acids in their cell walls. Bruckner et al. reported the presence of D-amino acids, including D-serine, in the urine from seven human subjects (Bruckner, et al., *Amino Acids* 1994. 6:205-211). Of the D-amino acids in urine, D-serine was present in the highest concentration (30 to 380 µMol/l). The percentage of D-serine relative to total (D-plus L-) serine ranged from 19% to 56%. Bruckner et al. speculated that D-amino acids in urine are derived from dietary sources (e.g., *Lactobacillus* in food).

It was recently reported that L-serine is converted to D-serine in mammalian brain by direct, enzyme-catalyzed racemization (Wolosker et al., PNAS 96:721-755, 1999). The highest concentrations of D-serine are found in regions of the brain having N-methyl-D-aspartate (NMDA) receptors for the neurotransmitter glutamate. D-serine functions as a potent agonist at the NMDA-glycine site and with glutamate can activate the NMDA receptor (Mothet et al. PNAS 97:4926-4931, 2000).

Uropathogenic *E. coli* are able to grow in media or urine in the presence of D-serine, whereas *E. coli* strains that lack the dsdCXA genes are unable to grow or grow more slowly than UPEC strains. As shown in the Examples below, three collections of *E. coli* were examined for the ability to utilize media having D-serine as the sole source of carbon and nitrogen. The results showed that 49 of 60 tested UPEC strains were able to use D-serine as the sole source of carbon and nitrogen. In contrast, just four of 74 tested hemorrhagic colitis and infantile diarrheal *E. coli* strains were able to use D-serine as the sole source of carbon and nitrogen.

As used herein, a "wild-type UPEC strain" is a strain of uropathogenic *E. coli* having the ability to use D-serine as the sole source of carbon and nitrogen.

To evaluate the role of the dsd operon in UPEC pathogenicity, a mutant in wild-type UPEC strain CFT073 with a deletion in the dsdA gene was constructed as described in the Examples. The dsdA mutant was evaluated for its ability to establish infection in a murine model of ascending urinary tract infection. Surprisingly, the mutant strain was present in the bladders and kidneys 48 hours postinfection at levels of about 300 times that of the wild-type strain. This result runs counter to our expectation that a knockout of this putative virulence gene would be less effective than wild-type CFT073 in establishing an infection. Complementation of the dsdA mutant with DsdA supplied in trans resulted in recovery similar to wild type.

The superior ability of the dsdA mutant over wild-type CFT073 to establish an infection in the murine coinfection experiments caused us to hypothesize that UPEC use D-serine as a signal to modulate growth and/or expression of virulence determinants. D-serine may act as an effector of the LysR-type transcriptional regulator, DsdC, to cause an increase in transcription. Production of DsdA would lower D-serine concentrations, which, if D-serine acts as an effector with DsdC, would reduce DsdC-regulated transcription. However, when concentrations of D-serine are relatively high, DsdC may remain active and cause the transcription of a myriad of genes for other virulence factors. It follows that people susceptible to recurrent UTIs caused by UPEC may produce urine with higher levels of D-serine than those who do not experience recurrent UTIs.

The identification of genes whose expression is regulated by D-serine, DsdC, or DsdC and D-serine will facilitate the design of drugs and methods of treating UTIs. Several approaches may be used to identify genes or proteins as targets for drug therapy.

One approach to identifying D-serine-regulated genes to create a library of transposon mutants by transposon-mediated mutagenesis, as described below in the Examples. Briefly, transposon mutagenesis is used to insert a gene encoding a detectable protein into the bacterial chromosome under the control of a transcriptional regulation sequence. Examples of suitable detectable proteins include, but are not limited to, luciferase and the lacZ gene product. Mutants expressing the detectable protein are identified and grown in the presence in or absence of D-serine. The relative expression of detectable protein in mutants grown in the presence and absence of D-serine is assessed, and those mutants exhibiting differential expression of the detectable protein in the presence and absence of D-serine are selected for further analysis.

Another approach to identifying genes whose expression is affected by DsdC or D-serine metabolism is to compare the proteins expressed by a wild-type UPEC strain grown in the presence or absence of D-serine, or expressed by a wild-type UPEC strain and a mutant of the strain comprising a mutation in dsdC, dsdA, or dsdX grown in the presence or absence of D-serine. Proteins are isolated from the bacterial cultures, separated by two-dimensional gel electrophoresis, and differential expression identified by comparing gels obtained from different bacterial strains or by the same bacterial strain grown in the presence or absence of D-serine. Proteins of interest may be further characterized to permit identification.

In another approach, RNA is isolated from a wild-type UPEC strain grown in the presence or absence of D-serine and subjected to reverse transcription to create labeled oligonucleotide probes, which in turn are hybridized to an oligomer array of *E. coli* gene sequences to identify sequences differentially expressed in the presence or absence of D-serine.

Using the methods described below in the Examples, several sequences differentially expressed in the presence of D-serine have been identified. Further identification and characterization of differentially expressed sequences is underway. Loss of function mutants for proteins identified as being of potential interest will be developed and evaluated for virulence using any suitable method. One method of evaluating virulence is an intracellular invasion assay, described in the Examples. Proteins that are correlated with virulence may be used to develop a vaccine against UPEC-mediated UTIs, to develop antibodies for use in treating UTIs by passive immunization, or to screen potential therapeutic agents. Conveniently, once a protein of interest is identified, the protein may be obtained by cloning the gene encoding the protein into an expression vector and obtaining expression in a suitable host cell.

The ability of certain UPEC strains to grow on D-serine will provide a simple means of differentiating *E. coli* isolates from urine or blood. The bacterial isolate may be tested for the ability to grow on or in medium containing D-serine as the sole carbon and nitrogen source. The bacterial isolate may be plated on a suitable medium comprising D-serine in a concentration effective to support growth of a UPEC strain capable of using D-serine as the sole source of carbon and nitrogen, suitably in the range of from about 100 ⊠g/ml to about 500 ⊠g/ml. Alternatively, an aliquot of the isolate may be transferred to a liquid medium comprising D-serine in an effective concentration, suitably in the range of from about 100 ⊠g/ml to about 500 ⊠g/ml. Growth in liquid medium may be assessed by observing turbidity. Optionally, the liquid medium may comprise an indicator such as tetrazolium, which undergoes a color change in response to bacterial growth. Alternatively, cells may be plated and then contacted with D-serine in a concentration effective to inhibit the growth of most non-UPEC isolates such as J198 (a normal fecal isolate), but which permits the growth of a wild-type UPEC strain such as *E. coli* strain CTF073. Conveniently, the D-serine may be delivered on a solid support, such as a filter disc of the type commonly used in antibiotic sensitivity testing, impregnated with D-serine.

Whether a correlation between UTI susceptibility and urinary D-serine levels exists may be determined by assaying D-serine in the urine of human populations having differential susceptibility to UTIs. If such a correlation exists, assaying D-serine may be useful in identifying individuals having this particular susceptibility. Unfortunately, D-serine assays are presently performed by HPLC and are prohibitively expensive for routine use.

The recognition that D-serine may play a role in establishing UTIs suggests the importance of having a simple assay for assaying D-serine levels. D-serine deaminase may be used to manufacture urine dipsticks and biosensors for quantifying D-serine. The D-serine deaminase may be coimmobilized on a suitable support with a suitable indicator that changes color in the presence of the ammonia generated by the enzymatic hydrolyis of D-serine. When the immobilized D-serine deaminase is exposed to a sample containing D-serine, the D-serine will be hydrolyzed to form pyruvate and ammonia, which will cause the indicator to change color, thus permitting the detection of the D-serine in the sample.

The D-serine deaminase used in urine dipsticks or biosensors may be obtained from any source. For example, D-serine deaminase may be obtained by subcloning a D-serine deaminase gene, such as the CFT073 dsdA gene (SEQ ID NO:6), into a suitable expression vector, introducing the vector into a suitable host cell, allowing expression of the protein, and recovering from the host cell D-serine deaminase substantially free of other proteins.

Suitable indicators include any compound that detectably changes in response to the hydrolysis of D-serine. For example, a suitable indicator may include an indicator that changes color in response to pH changes, which would occur with an increase in ammonia concentration. An example of such an indicator is phenol red.

The following non-limiting examples are intended to be purely illustrative.

EXAMPLES

Example 1

Bacterial Strains

Urosepsis *E. coli* strain CFT073 was originally isolated from the blood and urine of a woman admitted to the University of Maryland Medical System (Mobley et al., *Infect. Immun.*, 1990, 58: 1281-1289). *E. coli* strain collections used in epidemiology experiments were a collection of urosepsis and urinary tract isolates (Arthur et al., *Infect. Immun.*, 1989a, 57: 314-321; Arthur et al., *Infect. Immun.*, 1989b, 57: 303-313; Arthur et al., *Infect. Immun.*, 1990, 58: 471-479) and the DEC collection of hemorrhagic colitis and infantile diarrheal strains (Whittam et al., *Infection and Immunity*, 1993, 61: 1619-1629). Other strains used are described in Table 1: Bacterial strains and plasmids

TABLE 1

| Strains, plasmids | Description | Source or reference |
|---|---|---|
| Bacterial strains | | |
| S17-λpir | recA thi pro hsdR⁻ M⁺ (RP4-2 Tc::Mu-Km::Tn), λpir | (Simon et al., 1983) |
| CFT073 | urosepsis isolate | (Mobley et al., 1990) |
| CFT073 Nal$^R$ | urosepsis isolate; spontaneous Nal$^R$ | (Mobley et al., 1990) |
| WAM2615 | CFT073Δ –445 bp dsdA, Nal$^R$ | This study |
| WAM2692 | WAM2615 with pWAM2682 | This study |
| WAM2693 | CFT073 with pWAM2682 | This study |
| Plasmids | | |
| pEP185.2 | suicide vector, Cm$^R$ | (Kinder et al., 1993) |
| pWAM2682 | pACYC177, dsdA⁺, Kn$^R$ | This study |

Example 2

Media and Growth Conditions

To assess whether bacteria are able to utilize D-serine as the sole carbon and nitrogen source, bacteria were plated on a modified Minimal A Medium agar (15 g $K_2HPO_4$, 4.5 g $KH_2PO_4$, 1 g $K_2SO_4$, 0.5 g $Na_3C_6H_5O_7 \cdot 2H_2O$, 15 g agar and 1 ml of 1 M solution $MgSO4.7H_2O$ per liter) supplemented with 500 ug/ml of D-serine (Sigma) (Miller, *Experiments in molecular genetics*, 1972). For growth studies, bacteria were grown in MOPS minimal medium [3-(N-morpholino)propanesulfonic acid] supplemented with 10 μM thiamine and 0.4% glycerol (Neidhardt et al., *J. Bacteriol.*, 1974, 119: 736-747). For other experiments, the media used included L broth (5 g of sodium chloride, 5 g of yeast extract and 10 g of tryptone per liter [Fisher Scientific]) and L agar (L broth containing 1.5% agar [Difco]). Human urine was provided by two different donors and filter sterilized prior to use in experiments. Mouse urine was collected from a group of eight mice and UV sterilized prior to use. Antibiotics were added as needed at the following concentrations: nalidixic acid and kanamycin at 50 μg/ml and chloraramphenicol at 20 μg/ml (Sigma).

Liquid cultures were grown at 37° degrees with aeration except for cultures used in mouse UTI experiments. In the mouse UTI experiments, each strain was inoculated into L-broth and grown without aeration for two days. Bacteria were then passaged into fresh medium two additional times for a total of 6 days growth.

To determine growth curves, single colonies were inoculated into 5 ml of the appropriate medium and grown overnight at 37° C. with aeration. Following the overnight incubation, cells were collected by centrifugation, washed in saline and resuspended in 0.5 ml of saline (8.5 g NaCl per liter). The bacteria were then added to pre-warmed tubes of the desired medium. The $OD_{600}$ was adjusted to 0.03 with the appropriate medium. The cultures were grown at 37° C. with aeration and $OD_{600}$ readings were taken at the designated time points and dilutions were plated to determine CFUs.

Example 3

Construction of the dsdA Mutant

Restriction and DNA modification enzymes were purchased from either New England Biolabs or Promega Corporation. dsdA-specific primers for Polymerase Chain Reaction (PCR) were designed using the CFT073 genome sequence (R. A. Welch, unpublished). The dsdA primers used were 5'-GGATGGCGATGCTGCGTTG-3' (SEQ ID NO:11) and 5'-CACAGGGGAAGGTGAGATATGC-3' (IDT) (SEQ ID NO:12). The template was wild-type CFT073 genomic DNA prepared using the Wizard Genomic DNA Isolation Kit (Promega). The PCR amplification used the Expand High Fidelity PCR System (Roche Diagnostics) according to the manufacturer's protocol. The resulting PCR product was gel purified with the QIAQuick Gel Purification Kit (Qiagen) and ligated into pGEMt (Promega). The resulting dsda recombinant plasmid was examined by restriction endonuclease analysis. A dsdA deletion was constructed by digesting the dsdA plasmid with PmeI and EcoRI, which resulted in a 445 bp deletion. The digested plasmid was treated with T4 DNA polymerase in order to blunt the DNA ends. After gel purification, the plasmid was religated. An ApaI-SacI fragment containing dsda was subcloned into the suicide vector, pEP 185.2 (kind gift of Virginia Miller, Washington University). This construct was sequenced (ACGT, Incorporated) using T3 and T7 primers provided by ACGT. Conjugation was carried out as described by Kinder et al. (Kinder et al., *Gene*, 1993, 136: 271-275) with some modifications. The suicide plasmid construct was transformed into a S 17λpir background and then conjugated into a nalidixic acid resistant mutant of CFT073. Single-crossover chromosomal integrates of the recombinant plasmid were selected and D-cycloserine enrichment was used to select for a second crossover event that excised the suicide plasmid backbone from the CFT073 chromosome. Chromosomal DNA was isolated from the putative dsdA mutants and examined via PCR analysis using dsdA-specific primers to confirm the deletion. Phenotypic analysis of the putative mutants was carried out by inoculating colonies onto MOPS glycerol minimal and MOPS minimal D-serine agar media.

Example 4

Complementation of the dsdA Mutation

The dsdA gene, including its Shine and Delgarno sequence, was PCR amplified with primers (5'GCGCTG-CAGCGTTATTAACGGCCTTTTGCCA GATATTGATTC) (SEQ ID NO:17) and (5'CGCGGATCCCGTACTAT GGAAAACGCTAAAA TGAATTCGC) (SEQ ID NO:18). The primers were designed with PstI and BamHI restriction sites at their respective 5' ends. The PCR product was digested with PstI and BamHI enzymes, gel purified and ligated with pACYC177 previously digested with the same two restriction enzymes. The plasmid, designated pWAM2682, was used in subsequent complementation analysis.

Example 5

Mouse Model of Ascending UTI

After 6 days of static growth, the density of each bacterial strain was adjusted to an $OD_{600}$ of 0.6. Equal numbers of wild-type CFT073 cells and dsdA mutant (nalidixic acid resistant background) were mixed and pelleted by centrifugation for 15 min at 7000 rpm. The pellet was resuspended in 500 μl of phosphate buffered saline (7.5 g NaCl, 0.2 g KCl, 0.2 g $KH_2PO_4$, 1.15 g $Na_2HPO_4$ per liter). Female CBA/JCrHsd mice (five to eight weeks of age, Harlan) were inoculated via trans-urethral catheterization with 50 μl of the prepared bacteria (approximately $1 \times 10^9$ organisms). After 48 h, the mice were sacrificed and their bladders and kidneys harvested. The organs were homogenized and dilutions plated on L agar without antibiotics. After overnight incubation, colonies were counted and then replica plated onto L agar containing nalidixic acid in order to determine the number of surviving dsdA mutants. The nalidixic acid resistant CFT073 background strain used in the construction of the dsdA mutant competes equally with the CFT073 nalidixic acid sensitive parent strain in the UTI model (Torres et al., *Infect. Immun.*, 2001, 69: 6179-6185).

For the in vivo complementation studies, both the wild-type and dsdA mutant strains carried the complementing dsdA plasmid, pWAM2682. Both strains were grown as above with the addition of kanamycin in order to assure maintenance of the plasmids during the six day culture. Results were analyzed for statistical significance via paired Student's t test.

Example 6

Agglutination Assays to Measure Type 1 Fimbriae Expression

The wild-type and dsdA mutant strains were grown as described for the murine infection studies. The passaged cultures were diluted to an $OD_{600}$ of 0.6 and CFUs determined by plate count. The assay was carried out in a 96 well U-bottomed microtiter plate. Serial two-fold dilutions of each culture (50 µl) were mixed with 50 µl of a 25% suspension of guinea pig erythrocytes in saline. The mixtures were incubated at room temperature and agglutination titers were determined after 1.5 h. In these experiments, CFT073 mutants locked ON and locked OFF for type 1 fimbriae expression (N. W. Gunther, unpublished) were used as hemagglutination controls (kind gift of N. W. Gunther and H. L. Mobley).

Example 7

Microscopy

Wild-type and dsdA mutant strains grown overnight in human urine were inoculated into fresh urine and examined microscopically after 3 and 24 h of growth. The cell suspensions were air-dried on glass slides and stained with safranin. The cells were visualized using a Zeiss Axioplan IIi microscope and the images were collected digitally using OpenLabs 3.02 software (Improvision, Inc.).

Example 8

Isolation of a CFT073 lacZY Deletion Mutant

A CFT073 lacZY deletion mutant was isolated using the λ red recombinase mutagenesis system of Datsenko and Wanner (Datsenko et al., *Proc. Natl. Acad. Sci. USA*, 2000, 97(12): 6640-6645), which is incorporated by reference herein. Briefly, PCR products were generated using primers with 36- to 50-nucleotide extensions that are homologous to the region adjacent to the lacZYA genes and template plasmid carrying an antibiotic resistance gene flanked by FLP recognition target sites. The PCR product was introduced into CFT073 carrying a Red expression plasmid via electroporation. After selection, the resistance gene was eliminated introduction of a helper plasmid which acts directly on the FLP recognition target sites flanking the resistance gene. The temperature sensitive Red and FLP helper plasmids are cured by growth at 37 degrees C.

Example 9

Generation of Transposon Mutants Using miniTn10luxZY

MiniTn10lux transposon insertion mutants of CTF073 were constructed using miniTn10lux. *E. coli* strain KV330 (carrying the suicide plasmid pKV45 which harbors the miniTN10 transposon, transposase and resolvase) was the donor strain for conjugal transfer into recipient host strain CFT073. Transconjugants were plated on LB agar supplemented with chloramphenicol (to select for the transposon) and nalidixic acid (to select for the host strain, CFT073). Individual isolates were assayed for luciferase expression in the absence of presence of D-serine.

Example 10

Generation of Transposon Mutants Using miniTn5lacZY

MiniTn5lacZY transposon insertion mutants of a CFT073 lacZY deletion mutant were constructed as follows. *E. coli* S 17-1λpir containing the pREV 10 plasmid (this plasmid cannot be maintained in CFT073, but contains a MiniTn5 Km2 transposon with an added promoterless lacZY gene) was the donor strain for conjugal transfer into recipient strain, CFT073lacZYA. Transconjugants were plated on LB agar supplemented with kanamycin (to select for the transposon) and nalidixic acid (to select for the recipient strain, CFT073lacZYA). A library of these insertion mutants can then be screened for beta-galactosidase enzyme activity on either MOPS agar plates containing X-Gal (5-bromo-4-chloro-3-indoyl beta-D-galactoside) or standard MacConkey agar. On each of these medias, production of beta-galactosidase enzyme by bacterial colonies can be assayed by a color change. CFT-073lacZYA has no endogenous beta-galactosidase enzyme activity, so any detected activity is due to expression of genes near where the transposon has been inserted into the genome. Each insertion mutant can be grown on the two indicator medias in the presence or absence of 500 micrograms per milliliter D-serine. (Nelson K. M. et al., *Infect. Immun,*. 2001, 69(10):6201-6208.)

Example 11

D-Serine Utilization

Among the urosepsis and urinary tract isolates tested, 49 of 60 were able to grow on D-serrine minimal medium. In contrast, only four of the 74 strains from the DEC collection of hemorrhagic colitis and infantile diarrheal strains were able to grow on D-serine minimal medium.

Example 12

A CFT073 dsdA Mutant has a Prolonged lag Phase when Grown in Urine

Figures 2A, 2B:
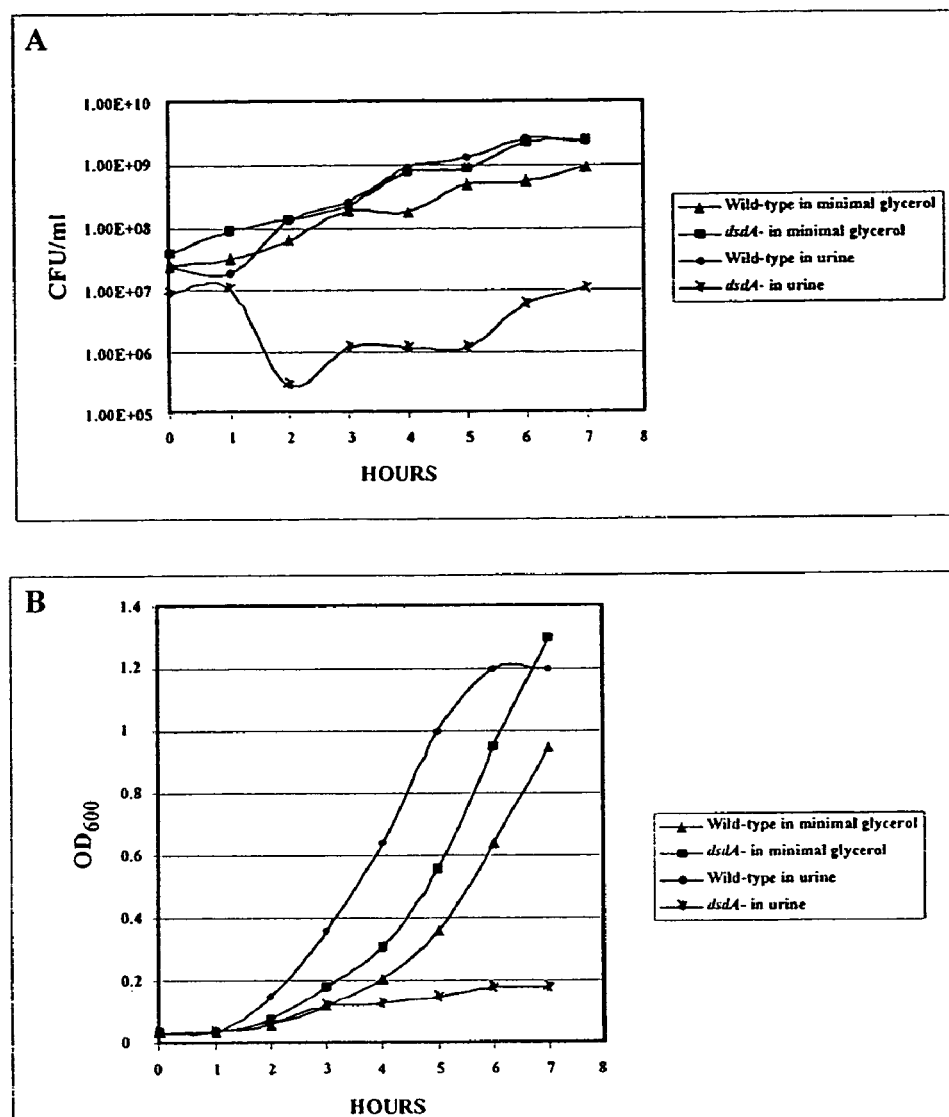
FIG. 2 compares the growth of wild type *E. coli* CFT073 or a dsdA mutant of *E. coli* CFT073 grown in minimal medium or urine as a function of time as measured by the concentration of colony forming units (2A) or the $OD_{600}$ (2B).

To evaluate the role of D-serine catabolism in uropathogenesis, a dsdA deletion mutant lacking the 445-bp corresponding to bases 18-486 of SEQ ID NO:5 was constructed as described above. The mutant, designated WAM2615, was found to lack the ability to grow on D-serine minimal medium. When DsdA was provided in trans, WAM2615 was able to grow on D-serine minimal medium. Growth of wild-type CFT073 and the dsdA mutant in glycerol minimal medium, human and mouse urine were compared. Neither wild-type CFT073 nor the dsdA mutant grew appreciably in mouse urine. The dsdA mutant grew at approximately the same rate as wild-type CFT073 in glycerol minimal medium, in which each had a doubling time of approximately 1.2 hours (FIG. 2A). However, when grown in human urine, the mutant exhibited a prolonged lag phase of approximately five hours, with an initial 10-fold decrease in colony-forming units (CFUs). At 10-12 h, the mutant then grew with wild type growth kinetics and after 11 h achieved CFUs equal to the wild-type (data not shown). The decrease in CFUs and prolonged lag phase was reproduced with the repeated subculture into fresh urine, which suggests that the resumption of growth was not due to acquired mutations (data not shown). Furthermore, when culture growth was monitored by $OD_{600}$, the initial decrease in CFUs exhibited by the dsdA mutant in urine was not accompanied by a concomitant decrease in optical density (FIG. 2B). The prolonged lag phase and loss of CFUs were abrogated when DsdA was provided in trans (data not shown). These results support the hypothesis that the ability to catabolize D-serine provides a growth advantage to UPEC in urine.

Example 13

Altered Cellular Morphology of dsdA Mutant Grown in Human Urine

The growth defect of the mutant in urine prompted a microscopic examination of its cellular morphology. Photomicrographs of the wild-type and mutant cells corresponding to the 3 h time point of the urine growth curve showed that the dsdA mutant lost the typical rod-shape seen with the wild-type and the pleiomorphic mutant cells were rounded and swollen. After 24 h in urine, the mutant cells became more rod-like and smaller in size. The cell shape defect observed for the mutant in urine was complemented when DsdA was provided in trans. When the mutant and wild-type were grown in L broth or glycerol minimal medium they appeared as rods that were similar in size (data not shown).

Example 14 dsdA Mutant Surpassed the Wild-Type Strain in Murine Model of UTI

Figures 3A, 3B:
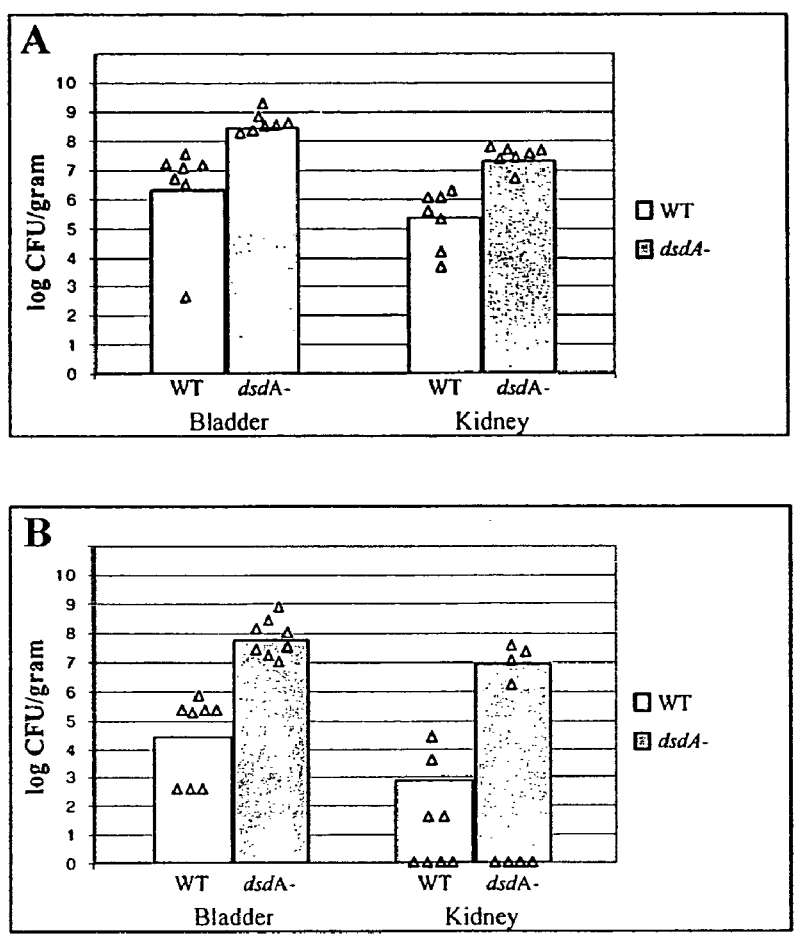
FIG. 3 compares the concentration of colony forming units of wild-type *E. coli* CFT073 or a dsdA mutant of *E. coli* CFT073 recovered from the bladder or kidneys of mice coinfected with mutant and wild-type *E. coli* CFT073.

The ability of dsdA mutant to establish infection was evaluated in a murine model of ascending UTI, as described above. Two days postinfection, the mutant was recovered at higher frequencies than the wild-type from both bladders and kidneys (FIGS. 3A and 3B). When two experiments were averaged, the recovered CFUs from the bladders and kidneys were approximately 270- and 300-times higher, respectively, for the mutant than the wild-type. The results were similar in an additional experiment where the tissues were harvested at eight days post-infection (data not shown). Overall, these results did not meet the expectation that the dsdA mutant would be less competitive than the wild-type in the UTI model. To examine the possibility that the strains differed in competitive growth ability, they were grown together in L broth, glucose minimal medium and glycerol minimal medium. There were no significant differences in growth or recovery rates of either the wild-type or the mutant in these media (data not shown).

Example 15 dsdA Gene Provided in trans Complements dsdA Mutation

Figure 4A:
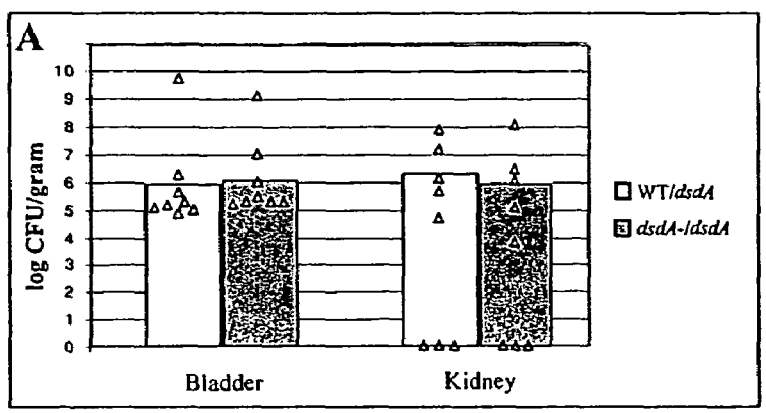
FIG. 4 compares the concentration of colony forming units of wild type *E. coli* CFT073 or a dsdA mutant of *E. coli* CFT073 recovered from the bladder or kidneys of mice coinfected with mutant and wild-type *E. coli* CFT073 strains carrying pWAM2682, which expresses DsdA in two replicate experiments (4A and 4B).
Figure 4B:
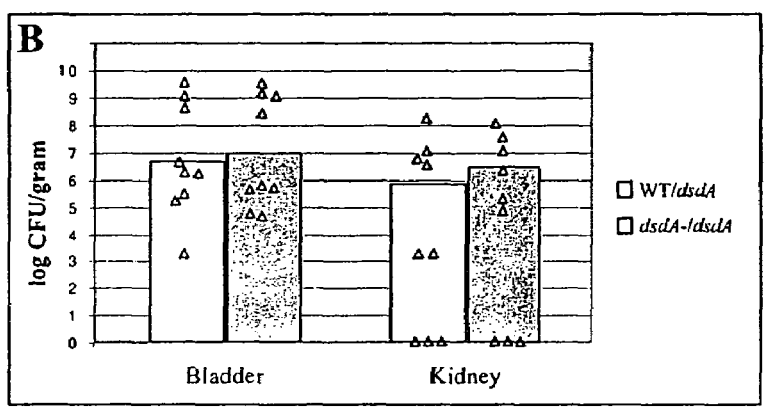
Figure 5:
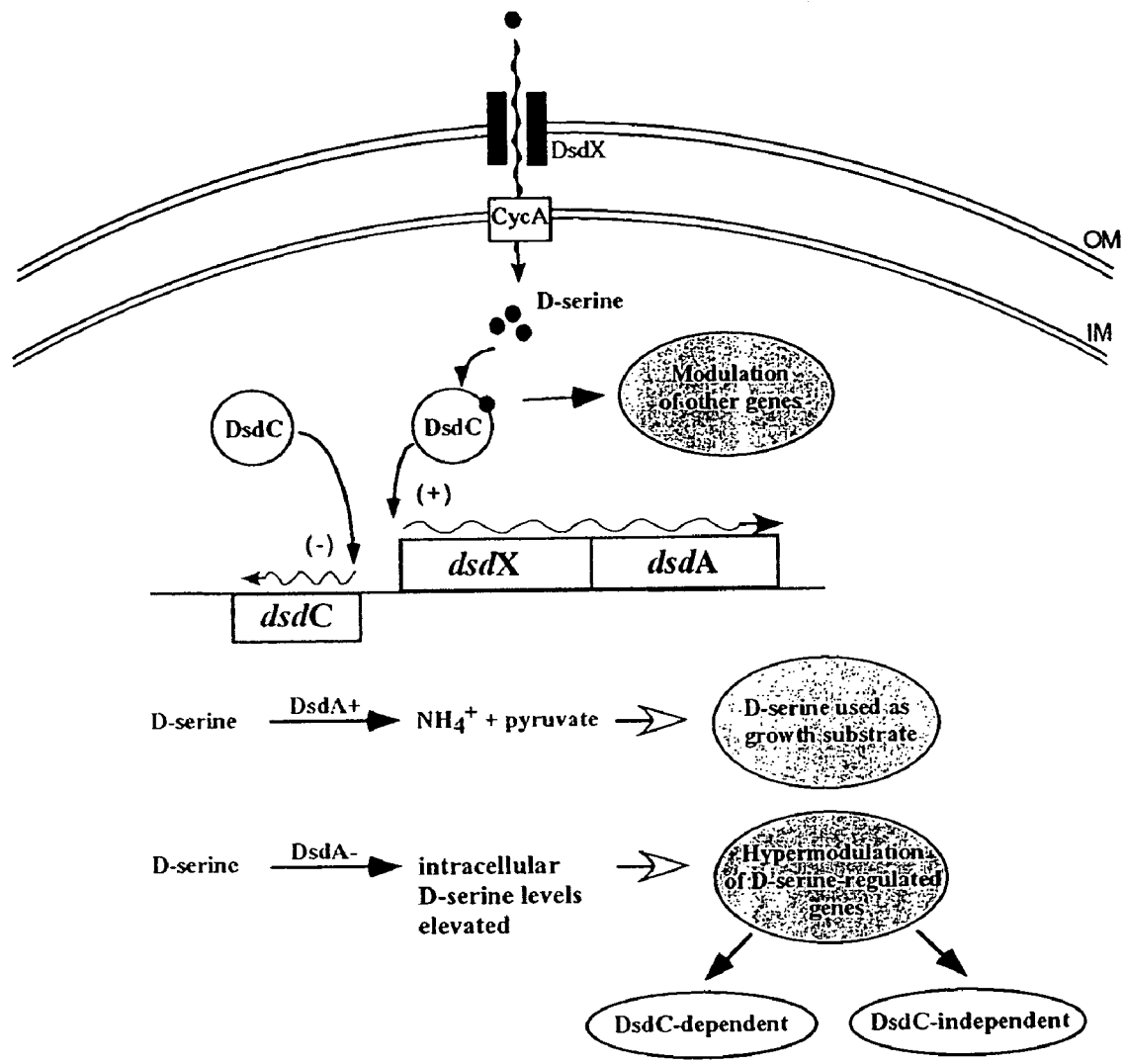
FIG. 5 presents a model D-serine modulation of *E. coli* uropathogenesis.

In order to rule out the possibility that unknown mutations in the dsdA mutant background were responsible for the competitive advantage, an intact dsdA gene was provided in trans. The complemented strain regained the ability to grow in D-serine minimal medium. For UTI experiments, the wild-type strain was transformed with the complementing plasmid in order to compensate for dsdA copy effects. When these strains were tested in the murine model, no statistically significant difference was observed in their recovery after a two day infection (FIGS. 4A and B).

Example 16

The Effect of the dsdA Mutation on UPEC Virulence Factors

Several groups have shown that expression of type 1 fimbriae is critical for establishing a UTI in different model systems (Connell et al., *PNAS*, 1996, 93: 9827-9832; Mulvey et al., *Science*, 1998, 282: 1494-1497; Sokurenko et al., *PNAS*, 1998, 95: 8922-8926). To determine if alterations in type 1 fimbrial expression were responsible for the dramatic effects of the dsdA mutation in vivo, type 1 fimbriae expression was assayed. In these experiments the wild-type and dsdA mutant strains were grown as described in Experimental procedures for the UTI studies. A pair of CFT073 mutants that are locked ON or locked OFF for expression of type 1 fimbriae (gift of Dr. Harry Mobley) were used as controls. The bacteria were diluted two-fold in microtiter wells and guinea pig erythrocytes were added to each well. The CFT073 type 1 locked ON strain had agglutination titers approximately two- to four-fold higher than wild-type CFT073. As expected, the CFT073 type 1 locked OFF mutant failed to agglutinate the erythrocytes. The agglutination titer for the dsdA mutant was two-fold less than the wild-type (data not shown).

Lipopolysaccharide was isolated from the wild-type and the dsdA mutant. No differences were observed in the relative amounts or sizes of their lipopolysaccharides. In addition, no differences were observed in the expression of hemolysin (data not shown).

Example 17

Identification of Mutants with Genes Differentially Expressed in Response to D-serine In order to identify genes with altered expression in response to the presence or absence of D-serine, a CFT073 library of random promoter probe miniTn10lux transposon insertions was constructed as described above. The transposon carries a promoterless luciferase gene that allows detection of loci potentially regulated by D-serine. Two thousand mutants grown on glycerol minimal medium in the presence or absence of D-serine, and observed for changes in light production using an X-ray film overlay.

The mutants demonstrating changes in light production were subsequently grown in glycerol medium liquid cultures and the levels of luminescence in the presence or absence of D-serine were quantitated. Four mutants with 3-fold or greater changes in luminescence were identified, and the sequence of the miniTn10lux insertion identified by subcloning and DNA sequence analysis. Using this approach for four mutants having increased expression of luciferase in the presence of D-serine, transposon insertions were found in the direction of transcription in coding sequence of genes. These genes were: yjiY, a MG1655 gene with weak sequence similarity with a carbon starvation protein; a MG1655 gene, manY involved in transport of mannose, ppsA (phosphoenolpyruvate synthase), an enzyme involved in gluconeogenesis, and an orf of unknown function. Interestingly, the unknown orf appears to be inserted within known genes involved in synthesis, secretion and immunity to the microcin H47, an antibiotic peptide produced by the H47 E. coli strain. Based on the comparison of the three E. coli genomes, the microcin 47 genes are present within a unique segment of CFT073 chromosome that is a new PAI present at the aspV tRNA site.

A CFT073 lacZY deletion mutant was used as the recipient for the miniTn5lacZY transposon to generate transposon mutants. To date, 2,000 colonies have been screened for changes in LacZ phenotypes. Twenty mutants having either increased or decreased LacZ expression upon exposure to non-inhibitory levels of D-serine (50 µg/ml) in complex media after overnight growth have been identified. The analysis of these mutants is underway.

The mutants will be subjected to Southern blotting analysis to assess the degree to which the insertions occur at different genomic locations. The insertion site for the D-serine regulated locus will be identified by either inverse PCR methods or direct selection of recombinant clones with the miniTn5lacZY kanamycin resistance gene and subsequent DNA sequence analysis of the transposon-chromosomal junction site using miniTn5lacZY termini-specific primers.

Example 18

Isolation of dsdXA Constitutive Promoter Mutants

Mutants in which expression of dsdC and dsdXA genes is independent of D-serine will be constructed by dsdC and dsdXA constitutive promoter mutations or by the recombinant construction of dsdC and dsdXA operons under the control of D-serine-independent, conditional promoters. D-serine deaminase constitutive mutants will be isolated as described by McFall et al. using chemical mutageneis and enrichment techniques in which D-serine is a growth limiting substrate (Bloom et al., *J. Bacteriol.*, 1975, 121: 1078-1084; Bloom et al., *J. Bacteriol.*, 1975, 121(3): 1092-1101; McFall, *Molecular Biology*, 1964, 9: 754-762; McFall, *J. Bacteriol.*, 1967, 94(6): 1982-1988; McFall, *J. Bacteriol.*, 1975, 121(3): 1074-1077; McFall, *J. Bacteriol.*, 1973, 113(2): 781-785; McFall et al., *Mol. Gen. Genet.*, 1970, 106(4): 371-377) which are incorporated by reference herein.

Alternatively, a mutant having D-serine-independent expression of the dsdCXA genes may be constructed from a mutant in which either the dsdC or dsdCXA promoter is deleted and replaced with a different promoter. Using the λ-red recombinase method, PCR-generated recombinant fragments encoding a tightly-controlled promoter such as the arabinose-inducible BAD promoter will replace the native promoter for independent control of transcription of either dsdC or dsdXA. Using this promoter will require controls that eliminate or minimize arabinose-specific effects outside of D-serine-affected sites. The native promoter-deletion mutant parent strain will be used under arabinose-inducing conditions as a control. Other suitable replacement promoters may include Class III-regulated CAP-cAMP promoter (MalT) or CAP-cAMP independent, inducible promoters. With the above constructs the expression of dsdC or dsdXA can be put under DsdC-D-serine-independent control.

Using either the constitutive promoter mutants or BAD-dependent constructs, loss of function mutations for each dsdCXA gene alone and selected combinations will be constructed. This will permit examination of a variety of phenotypes independent of D-serine-induced expression. For example, dsdA and dsdA-dsdC double mutants in these backgrounds would enable study of dsdA phenotypes that are either dsdC-dependent or -independent. In addition, in a dsdC mutant where dsdXA is under D-serine independent expression, possible D-serine transport via DsdX can be studied without the changes in DsdX expression.

Example 19

Identification of dsdC-dependent and -independent/D-serine Regulated Genes

Genetic screening to identify dsdC-dependent and -independent/D-serine regulated genes will involve assessing LacZ phenotypic changes in a miniTn5 lacZY CFT073 mutant library in which dsdC is under control of a conditional promoter. This strategy was used to identify RscR-regulated genes in *Y. enterocolitica* (Nelson, et al., 2001). However, in our system, the D-serine transporter gene, dsdx must be under transcriptional control that is independent of dsdC and D-serine. A dsdA deletion will be introduced into a dsdXA constitutive promoter mutant isolated as described above. The cellular D-serine levels can be controlled in such a mutant during in vitro growth. Alternatively, starting with a CFT073 dsdXA deletion mutant background, dsdx would be reinserted, but under control of an independent constitutive promoter. For the conditional expression of dsdC, a dsdC deletion mutant of either of the previous dsdX constructs will be complemented by a dsdC recombinant plasmid with dsdC under control of the araBAD ($P_{bad}$) promoter from vectors pBAD18 or pBAD33 (Guzman, et al., *J. Bacteriol.*, 1995, 177(14): 4121-4130). CFT073 LacZ transcriptional fusion mutants altered in expression in the presence of arabinose and D-serine will be quantified by β-galactosidase assays. Mutants with 3-fold or greater changes in β-galactosidase activity in the presence of D-serine and arabinose will be chosen for further study. A secondary screen will identify the fusions that are independent of dsdC and controlled by D-serine alone. The dsdC-recombinant plasmid from the mutants will be cured by repeated rounds of nonselective growth as done by Nelson et al. (Nelson et al., 2001) The cured mutants will be assessed for retention of the D-serine-specific phenotype. Those mutants that are regulated by arabinose alone will be eliminated from further study. Transposon insertion sites of mutants specific for dsdC or D-serine will be identified as described above.

Example 20

Identification of Differentially Expressed Proteins

Protein expression of wild type CFT073 and CFT073 dsdA mutant grown in human urine and glycerol minimal medium plus or minus D-serine will be compared. Total and envelope-enriched cellular proteins will be separated by two-dimensional electrophoresis (Kendrick Labs, Madison, Wis.). Samples will be prepared in triplicate and subjected to independent electrophoretic runs. Individual polypeptide spots will be isolated. Polypeptide species with reproducible changes in expression levels in response to loss of DsdA will be identified by MALDI-TOF mass spectrometric identification of peptides by molecular weight (Kendrick Labs, Madison, Wis.).

Example 21

Identification of Differentially Expressed Genes Using Microarrays

Microarray techniques will be used to assess the patterns of genome-wide gene expression controlled by D-serine (+/−) DsdC. The initial comparative analysis will use RNA purified from CFT073 cells grown in glycerol minimal medium (+/−) D-serine. Initially studies will use the *E. coli* K-12 spotted orf arrays, which are available from the University of Wisconsin Gene Expression Center (GEC) (http://www.gcow.wisc.edu/gec/index.html) (Wei et al., *J. Bacteriol.*, 2001, 183(2): 545-556). Based on preliminary data, it is expected that CFT073 cells grown in minimal glycerol medium (+/−) D-serine will show expression differences for at least dsdXA, ppsA and manY, where those genes are represented on the *E. coli* K-12 arrays. These genes will serve as positive controls. CFT073-specific oligomer arrays will be made at the UW Gene Expression Center by the NimbleGen technology, a maskless array synthesizer that produces 125,000 custom oligonucleotide arrays with 20 base oligomers present at 16 μm×16 μm spots.

Microhybridization will be performed according to the protocol provided by GEC. Labeled probes will be generated starting with total RNA extracted from bacteria by the method described by the Gene Expression Center. Cells harvested from liquid cultures are treated with one part boiling lysis solution (2% SDS, 16 mM EDTA, 200 mM NaCl) to two parts culture solution and boiled for 5 minutes with vortexing. This aqueous solution will then be extracted three times with hot acid-phenol-chloroform and once with chloroform-isoamyl alcohol. Total RNA will be precipitated with isopropanol overnight at −20° C. and washed once with cold 70% ethanol. RNA samples will then be resuspended in DEPC-treated water and treated with RNase free RQ1 DNase (Promega). Each reaction will be then re-purified using an RNeasy kit (QIAgen) and further precipitated with lithium chloride (Ambion) according to each Manufacturer's protocol. Samples will be resuspended in DEPC-treated water and the concentration and purity of each determined by absorbance at 260/280 nm. Integrity of the rRNA bands will be determined by running each sample on a formaldehyde-agarose gel.

Samples of total RNA will be labeled with either Cy5- or Cy3-labeled dUTP (Amersham-Pharmacia) according to the protocol supplied by GEC. Briefly, 20 μg of each sample will be mixed with 10 μg of random hexamer primers (Amersham-Pharmacia), heated to 70° C. for 5 minutes, then placed on ice. The 1X labeling mixture (containing first strand buffer [GibcoBRL], DTT, deoxynucleoside triphosphates [low dTTP, Promega], RNAsin [Promega] and DEPC water) will be added to each sample and incubated at room temperature for 10 minutes. Cy5-dUTP (or Cy3-dUTP)-labeled cDNA will be generated by reverse-transcription with Superscript II (GibcoBRL) at 42° C. for 2 hours in the dark. After labeling, remaining RNA will be hydrolyzed by the addition of NaOH and incubation for 15 minutes at 65° C. followed by the addition of HCl and Tris (pH 7.4) to neutralize the reactions. Control and experimental probes will be purified, combined, and concentrated using Microcon MY-30 filter units (Amicon).

The labeled probes will be mixed with one μg salmon sperm DNA, 4 μg of yeast tRNA and 10 μl of PerfectHyb Plus hybridization buffer (Sigma) to a final volume of 20 μl. This mixture will be heated for 5 minutes at 100° C. and hybridized to the microarray overnight (~16 hours at 60° C.). Microarrays will then be washed 2 minutes in 0.2×SSC, 0.1% SDS, followed by two washes in 0.2×SSC, and a final wash in 0.05×SSC for 15 seconds.

Hybridization slides will be dried by centrifugation and immediately scanned using a Packard BioChip SA5000 scanning system. This system includes a scanning laser confocal fluorescence microscope and the ScanArray software that collects the 16-bit TIFF images. These images will be quantified using the QuantArray software, which automates spot finding and allows the quantitation of spot intensity.

Induction ratios for each gene will be calculated by dividing background-adjusted intensities of the experimental sample by the background-adjusted intensities of the control sample. The intensities used for these calculations will be expressed as a percentage of the total intensity of all the spots on each array, which corrects for the specific activity of probes used between arrays. Those genes having induction ratios of greater than 2 standard deviations from the mean induction ratio will be selected for further analysis and confirmation by Northern analysis.

Currently, most array data are analyzed by observing the level of induction and choosing an arbitrary cut-off point for significance. The GEC is investigating more rigorous and computationally intense methods of array data analysis. DNA microarray experiments are expensive, so replication of experiments needs to be minimized. To address this, a Bayesian statistical approach that includes prior information about the arrays (from previous experiments) in weighting the expression ratios can be used to improve the confidence of measurements (Long et aL, *J. Biol. Chem.*, 2001, 276(23): 19937-19944). Software that applies this method, Cyber-T, is available freely from the genomics web site at the University of California at Irvine (Long et al., 2001).

Northern blotting or primer-extension analysis will be used to confirm the change in transcription levels. Candidate genes that are altered in their expression upon exposure to D-serine will be assessed for likelihood of their impact on uropathogenesis. Solid candidate genes will be mutagenized and mutants assessed for their competitive ability against the CFT073 wild type strain in the mouse UTI model.

Example 22

Differential Fluorescence Induction (DFI) in the Presence and Absence of D-serine In our laboratory, the Valdivia and Falkow DFI technique (Valdivia, et al., *Science,* 1997, 277: 2007-2011) permitted identification of 12 CFT073 genes that are up-expressed in the peritoneal cavity of mice but down-expressed during growth in L-broth. We constructed two separate CFT073 libraries containing 1-3 kb partial Sau3A digest fragments inserted into the promoterless GFP vector, BVC. We will reuse the libraries to identify promoters that are negatively or positively affected by growth in the presence of D-serine. This approach will identify genes that undergo relatively large changes in their expression under the alternative conditions (presence or absence of D-serine). The DFI method may also be applied with a new library constructed in a CFT073 dsdA mutant background. This new library would then be put through selections of either growth in human urine or infected mouse bladders or kidneys in the UTI model. The D-serine-positive genes that are selected and eventually identified by DNA sequence analysis will be subjected to Northern blotting analysis to confirm the induction of steady-state levels of gene-specific mRNA. Based on the criteria described above, candidate genes will be chosen for mutant construction and phenotypic analysis.

Example 23

Binding of DsdC-D-serine to Promoter Regions of Gene Sequences

Direct binding of DsdC to candidate genes will be evaluated in the presence and absence D-serine. DsdC will be obtained from cellular extracts from strains in which DsdC is constitutively expressed or over expressed in vectors such as pT7 in a BL21 (DE3) pLysS background (Novagen). Candidate promoter fragments will be synthesized by PCR amplification, labeled internally with [$\alpha$-$^{32}$] dNTP or terminally by [$\gamma$-$^{32}$] dNTP, and purified. The labeled promoter fragments will be incubated in binding reactions including variables as described in Ausubel et al (Ausubel et al., *Current Protocols in Molecular Biology*, 1987, New York: John Wiley and Sons). Sample mixtures will be separated by nondenaturing polyacrylamide gel electrophoresis and the radiolabeled bands identified by autoradiography. If warranted based on the perceived importance of the identified targets to uropathogenesis, we will purify reagent amounts of DsdC for more detailed studies. DsdC will be acquired by standard overexpression vector technology or gene fusion affinity chromatography methods. To more precisely map the DsdC binding sites, the purified DsdC (+/−D-serine) will be used in DNA mobility shift (gel-retardation) assays with overlapping PCR fragments and DNase I footprinting methods (Ausubel et al., 1987).

Binding of DsdC protein to nucleotide sequences could also be detecting by labeling the DsdC protein with a detectable label, using the labeled DsdC to probe of an oligomer array of nucleotide sequences from a UPEC strain, detecting binding of DsdC to oligomers, and identifying the oligomer. The binding assays may be performed in the presence or absence of D-serine.

In vitro transcription reactions will be performed as described previously (Aiyar et al., *PNAS*, 1998, 95(25): 14652-14657; Weyand et al., *Mol. Microbiol.*, 2001, 39(6): 1504-1522), in the presence and absence of D-serine. These experiments will permit identification of newly synthesized labeled transcripts by gel electrophoresis and autoradiography. McFall's group demonstrated that D-serine deaminase activity could be detected in DsdC-dependent in vitro transcription/translation reactions using recombinant plasmids (Heincz et al., *J. Bacteriol.*, 1984, 160(1): 42-49). This result suggests that in vitro transcriptional analysis with DsdC-dependent promoters is feasible.

Example 24

Evaluation of D-serine Regulated Genes in Pathogenesis

To directly assess the relevance of the D-serine-regulated genes that are identified, loss-of-function, in-frame deletion mutants will be constructed utilizing the PCR fragment λ-red recombinase method (Datsenko et al., 2000) and tested for the ability to compete with CFT073 wild type in the UTI model as described above.

Intracellular invasion assays of 5637 human bladder epithelial cells as described by Mulvey et al. (Mulvey et al., *Science*, 1998, 282(5393): 1494-1497; Mulvey et al., *Infect. Immun.*, 2001, 69(7): 4572-4579), which are incorporated by reference herein, will be performed to compare the abilities of the CFT073 and CFT073 dsdA strains to invade and replicate.

We have acquired from Dr. Scott Hultgren, *E. coli* strain NU14 will be used as a positive control in the invasion studies. In addition, two CFT073 mutants that are locked "ON" or "OFF" will be included as controls for type 1 pili expression and mannose-sensitive guinea pig RBC-agglutination activity. These strains were the kind gift of Dr. Harry Mobley. The CFT073 type 1 pilus "OFF" mutant should serve as the negative control for the invasion studies. We expect that these experiments will help to assess if the 300-fold greater competitive ability of the CFT073 dsdA mutant is correlated with either increased efficiency in attachment, intracellular invasion or intracellular persistence. The latter phenotype will be judged to occur if intracellular organisms do not decrease over time or there appears to be decrease in the killing of the cells in the infected epithelial cell layers. The uroepithelial invasion assay will be used to assess the phenotypes of the additional mutants isolated as described above.

The present invention is not limited to the exemplified embodiments, but is intended to encompass all such modifications and variations as come within the scope of the following claims.

PUBLICATIONS CITED

Aiyar, S. E., et al., *PNAS*, 1998, 95(25): 14652-14657.
Arthur, M., et al., *Infect. Immun.*, 1989a, 57: 314-321.
Arthur, M., et al., *Infect. Immun.*, 1989b, 57: 303-313.
Arthur, M., et al., *Infect. Immun.*, 1990, 58: 471-479.
Ausubel et al., *Current Protocols in Molecular Biology*, 1987, New York: John Wiley and Sons.
Bloom, F. R., et al., *J. Bacteriol.*, 1975, 121:1078-1084.
Bloom, F. R., et al., *J. Bacteriol.*, 1975, 121(3): 1092-1101.
Bruckner, J., et al., *Amino Acids*, 1994, 6: 205-211.
Connell, J., et al., *Proc. Natl. Acad. Sci. USA* 1996, 93: 9827-9832.
Datsenko, K., et al., *Proc. Natl. Acad. Sci. USA*, 2000, 97(12): 6640-6645.
Guzman, L., et al., *J. Bacteriol.*, 1995, 177(14): 4121-4130.
Heincz, M. C., et al., *J. Bacteriol.* 1984, 160: 42-49.
Kinder, S. A., et al., *Gene*, 1993. 136: 271-275.
Long, A. D., et al., *J. Biol. Chem.*, 2001, 276(23): 19937-19944.
McFall, E., *Molecular Biology*, 1964, 9: 754-762.
McFall, E., *J. Bacteriol.* 1967, 94: 1982-1988.
McFall, E., *J. Bacteriol.*, 1975, 121(3): 1074-1077.
McFall, E., *J. Bacteriol.*, 1973, 113(2): 781-785.
McFall, E., et al., *Mol. Gen. Genet.*, 1970, 106(4): 371-377.
Miller, J. H., *Experiments in molecular genetics*, 1972.
Mobley, H. L., et al., *Infect. Immun.*, 1990, 58: 1281-1289.
Mothet, J. P., et al., *Proc. Natl. Acad. Sci. USA*, 2000, 97: 4926-4931.
Mulvey, M. A., et al., *Science*, 1998, 282: 1494-1497.
Mulvey, M. A. et al., *Infect Immun.*, 2001, 69(7): 4572-4579
Neidhardt, F. C., et al., *J. Bacteriol.*, 1974, 119: 736-747.
Nelson, K. M., et al., *Infect. Immun.*, 2001, 69: 6201-6208.
Simon, R., et al., *Biotechnology*, 1983, 1: 784-791.
Sokurenko, E. V., et al., *Proc. Natl. Acad. Sci. USA*, 1998, 95: 8922-8926.
Torres, A. G., et al., *Infect. Immun.*, 2001, 69: 6179-6185.
Valdivia, R. H., et al., *Science*, 1997, 277: 2007-2011.
Wei, Y., et al., *J. Bacteriol.*, 2001, 183(2): 545-556.
Weyand, N. J., et al., *Mol. Microbiol.*, 2001, 39(6): 1504-1522.
Whittam, T. S., et al., *Infect. Immun.*, 1993, 61: 1619-1629.
Wolosker, H., et al., *Proc. Natl. Acad. Sci. USA*, 1999b, 96: 721-725.

We claim:

1. A method of characterizing an *E. coli* strain isolated from a clinical sample comprising testing the strain for the ability to grow in the presence of D-serine.

2. The method of claim 1, wherein D-serine is the sole source of carbon and nitrogen.

3. The method of claim 1, wherein D-serine is present in a concentration effective to inhibit the growth of a normal fecal isolate of *E. coli*.

4. The method of claim 1, wherein D-serine is present in a concentration of at least 100 μg/ml.

5. The method of claim 1, wherein D-serine is present in a concentration of from about 100 μg/ml to about 500 μg/ml.

6. The method of claim 1, wherein the clinical sample is urine.

7. The method of claim 1, wherein the clinical sample is blood.

* * * * *